(12) United States Patent
Yamamoto et al.

(10) Patent No.: US 10,786,204 B2
(45) Date of Patent: Sep. 29, 2020

(54) ELECTRONIC DEVICE

(71) Applicant: Kabushiki Kaisha Toshiba, Minato-ku, Tokyo (JP)

(72) Inventors: Nobuhiro Yamamoto, Yokohama Kanagawa (JP); Takahisa Funayama, Musashino Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1274 days.

(21) Appl. No.: 14/979,045

(22) Filed: Dec. 22, 2015

(65) Prior Publication Data

US 2017/0035356 A1 Feb. 9, 2017

Related U.S. Application Data

(60) Provisional application No. 62/200,351, filed on Aug. 3, 2015.

(51) Int. Cl.
| | |
|---|---|
| *A61B 5/00* | (2006.01) |
| *A61B 5/053* | (2006.01) |
| *A61B 5/0245* | (2006.01) |
| *A61B 5/024* | (2006.01) |
| *A61B 5/0402* | (2006.01) |
| *A61B 5/11* | (2006.01) |

(52) U.S. Cl.
CPC .......... *A61B 5/6844* (2013.01); *A61B 5/0245* (2013.01); *A61B 5/02433* (2013.01); *A61B 5/0402* (2013.01); *A61B 5/053* (2013.01); *A61B 5/1117* (2013.01); *A61B 5/6823* (2013.01); *A61B 2562/0219* (2013.01)

(58) Field of Classification Search
CPC ..... A61B 5/0205; A61B 5/0402; A61B 5/024; A61B 5/0006; A61B 5/6844
USPC ................ 600/300, 301, 508, 509, 513, 547
See application file for complete search history.

(56) References Cited

U.S. PATENT DOCUMENTS

| | | | |
|---|---|---|---|
| 8,655,443 B2* | 2/2014 | Brunswick | ............... A61B 5/05 600/382 |
| 8,731,657 B1* | 5/2014 | Shambayati | ....... A61N 1/36014 128/908 |
| 9,474,898 B2* | 10/2016 | Gozani | ..................... A61N 1/08 |
| 2009/0259124 A1* | 10/2009 | Rothenberg | ......... A61B 5/0452 600/424 |
| 2012/0296571 A1 | 11/2012 | Shinoda et al. | |
| 2013/0218067 A1* | 8/2013 | Saito | ...................... A61N 1/303 604/20 |
| 2014/0275823 A1* | 9/2014 | Lane | .................. A61B 5/04087 600/301 |

(Continued)

FOREIGN PATENT DOCUMENTS

| | | |
|---|---|---|
| JP | 2004-000333 A | 1/2004 |
| JP | 2007-319506 A | 12/2007 |
| JP | 5692097 B2 | 4/2015 |

*Primary Examiner* — John R Downey
(74) *Attorney, Agent, or Firm* — White & Case LLP

(57) ABSTRACT

According to one embodiment, an electronic device includes an attaching member and a sensing circuit. The attaching member includes a face configured to be attached to a detection target. The sensing circuit includes a sensing interface provided on the face. The sensing circuit is configured to obtain information related to a contact state between the sensing interface and the detection target from the sensing interface.

13 Claims, 14 Drawing Sheets

(56) References Cited

U.S. PATENT DOCUMENTS

| | | | | |
|---|---|---|---|---|
| 2014/0275849 A1* | 9/2014 | Acquista | .............. | A61B 5/0022 |
| | | | | 600/301 |
| 2016/0095527 A1* | 4/2016 | Thng | .................... | A61B 5/6808 |
| | | | | 600/301 |
| 2017/0238812 A1* | 8/2017 | Atlas | ....................... | G16H 40/67 |
| 2017/0356815 A1* | 12/2017 | Madden | ................ | G01L 1/2287 |

\* cited by examiner

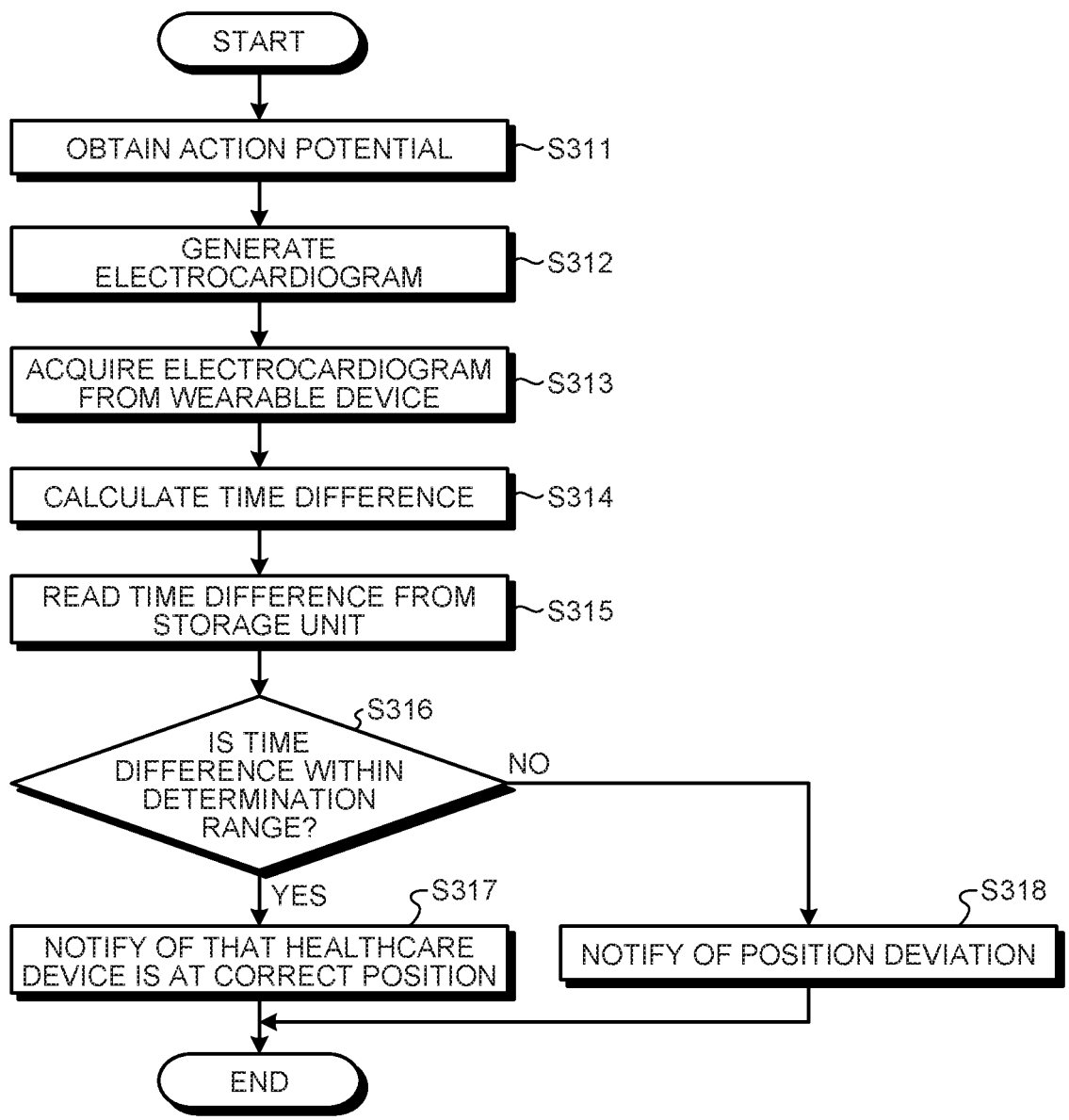

ELECTRONIC DEVICE

CROSS-REFERENCE TO RELATED APPLICATIONS

This application is based upon and claims the benefit of priority from U.S. Provisional Application No. 62/200,351, filed on Aug. 3, 2015; the entire contents of which are incorporated herein by reference.

FIELD

Embodiments described herein relate generally to an electronic device.

BACKGROUND

An electronic device such as a wearable device that senses biological information of a user wearing the electronic device is known.

BRIEF DESCRIPTION OF THE DRAWINGS

FIG. 17 is a flowchart illustrating a part of a mounting position detection process performed by the healthcare device according to the third embodiment.

DETAILED DESCRIPTION

In general, according to one embodiment, an electronic device including an attaching member and a sensing circuit is provided. The attaching member includes a face configured to be attached to a detection target. The sensing circuit includes a sensing interface provided on the face. The sensing circuit is configured to obtain information related to a contact state between the sensing interface and the detection target from the sensing interface.

Exemplary embodiments of an electronic device will be explained below in detail with reference to the accompanying drawings. The present invention is not limited to the following embodiments.

First Embodiment

Hereinafter, a first embodiment will be described with reference to FIGS. 1 to 10. A plurality of expressions may be used for an element according to an embodiment or a description of the element. Another expression that is not described may be used for the element and a description thereof. Another expression may be used for the elements and a description thereof in which a plurality of expressions are not described.

Figure 1:
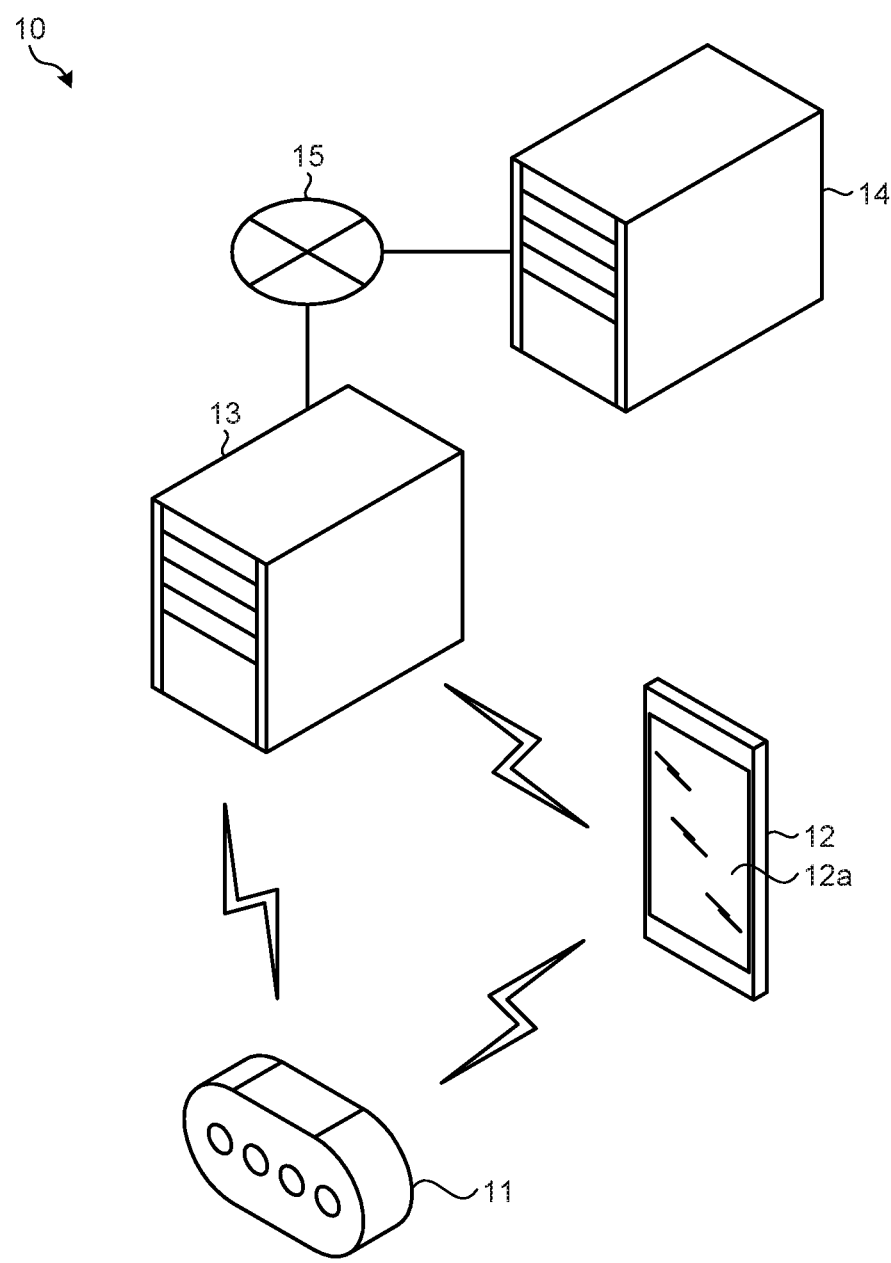
FIG. 1 is a diagram schematically illustrating a configuration of a monitoring system according to a first embodiment.

FIG. 1 is a diagram schematically illustrating a configuration of a monitoring system 10 according to a first embodiment. The monitoring system 10 is configured such that a healthcare device 11, an information terminal 12, a plurality of first servers 13, and a plurality of second servers 14 are connected as illustrated in FIG. 1. In FIG. 1, one first server 13 and one second server 14 are illustrated.

The healthcare device 11 is an example of an electronic device, and can also be referred to as, for example, a wearable device, a monitoring device, a sensor, an apparatus, or a device. Each of the information terminal 12 and the first server 13 is an example of another device. The information terminal 12 can also be referred to as, for example, an electronic device, a computer, a terminal, a display device, an apparatus, or a device. Each of the first and second servers 13 and 14 can also be referred to as, for example, a computer, a control device, an apparatus, or a device.

The healthcare device 11, the information terminal 12, and the first server 13 are connected directly or through a relay device such as a router via a wireless network such as a wireless LAN, a Bluetooth (a registered trademark), or a third generation mobile communication system (3G) or connected via a public network 15 such as the Internet. The plurality of first servers 13 are connected to the plurality of second servers 14, for example, via a public network 15.

For example, the healthcare device 11 according to the present embodiment is attached to the chest of the user. For example, the healthcare device 11 detects the heart rate of the user. The healthcare device 11 according to the present embodiment can transmit information related to the detected heart rate to the information terminal 12 and the first server 13 directly or via a relay device.

The information terminal 12 is a smartphone as illustrated in FIG. 1, for example. The information terminal 12 is not limited to this example and may be any other device such as a mobile phone, a tablet device, a wearable device, a portable computer, a personal digital assistant (PDA), a personal computer, or a television receiver device, for example.

The information terminal 12 may be owned by the user or may be owned by any other person (hereinafter, referred to as an "observer") such as a family member of the user or a doctor. The following description will proceed with an example in which the information terminal 12 is owned by the observer. Each of the user and the observer may own the information terminal 12.

The information terminal 12 includes a display unit 12a. For example, the display unit 12a is a part displaying an image such as a liquid crystal display (LCD) or an organic EL display. For example, the display unit 12a can also be referred to as an output unit. The information terminal 12 displays, for example, the information related to the heart rate of the user received from the healthcare device 11 through the display unit 12a. The observer can observe the heart rate of the user through the information terminal 12.

The first server 13 processes, for example, the information related to the heart rate of the user received from the healthcare device 11. For example, when there is an abnormality in the information related to the heart rate of the user, the first server 13 may notify the information terminal 12 of an abnormality.

For example, the second server 14 extracts predetermined information from the information related to the heart rate of a plurality of users received by the plurality of first servers 13, and processes the extracted information. The second server 14 may detect an abnormality in the information related to the heart rate of the user by performing integrated determination based on the extracted information. When there is an abnormality in the information related to the heart rate of the user, the second server 14 may notify the information terminal 12 of the abnormality.

Figure 2:
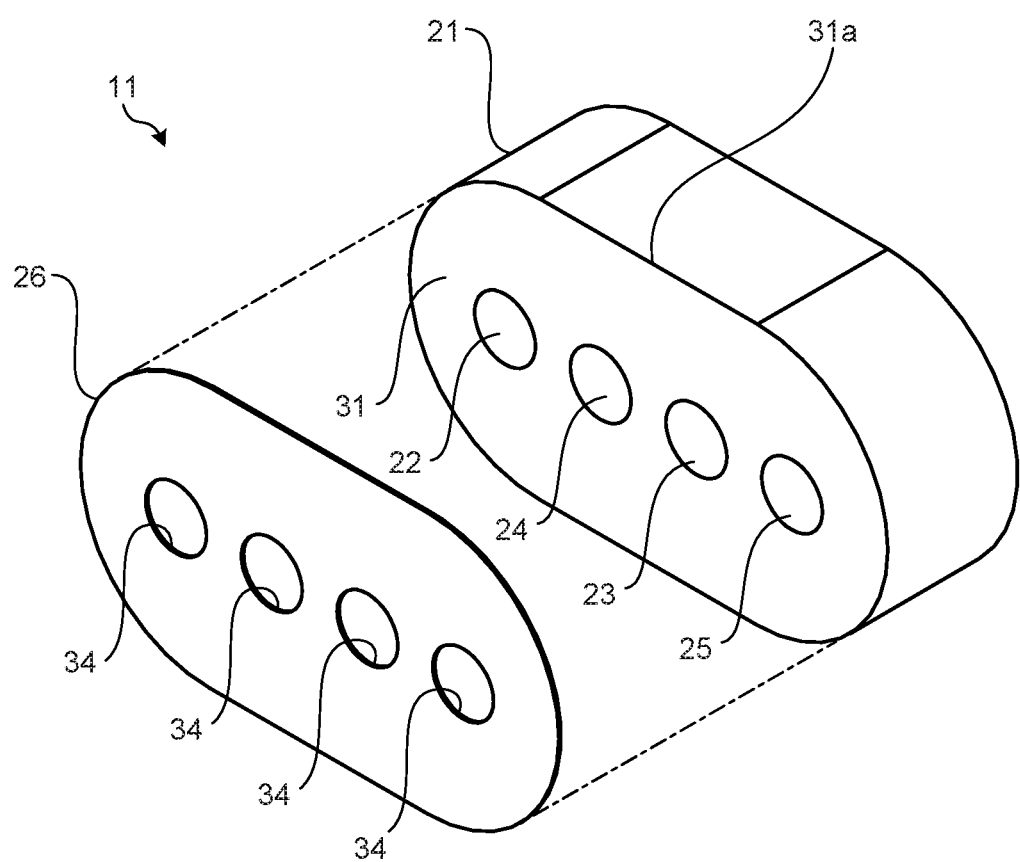
FIG. 2 is a perspective view illustrating a healthcare device according to the first embodiment.

FIG. 2 is a perspective view illustrating the healthcare device 11 according to the first embodiment. The healthcare device 11 includes a housing 21, a first positive electrode 22, a second positive electrode 23, a first negative electrode 24, a second negative electrode 25, and a double-sided tape 26 as illustrated in FIG. 2.

The housing 21 is an example of an attaching member and can also be referred to as, for example, a base, an exterior part, a wall, a part, or a portion. The first positive electrode 22 is an example of a sensing interface, an electrode, a first sensing interface, and a first electrode. The second positive electrode 23 is an example of a sensing interface and an electrode. The first negative electrode 24 is an example of a sensing interface, an electrode, a first sensing interface, and a second electrode. The second negative electrode 25 is an example of a sensing interface and an electrode. Each of the first positive electrode 22, the second positive electrode 23, the first negative electrode 24, and the second negative electrode 25 can also be referred to as, for example, a terminal or a conductive portion.

For example, the housing 21 is made of synthetic resin. The housing 21 may be made of any other material such as metal or ceramics. The housing 21 includes an attaching face 31. The attaching face 31 is an example of a face and can also be referred to as, for example, a mounting part or portion.

The attaching face 31 is formed in an oval shape and has a substantially flat surface. The attaching face 31 may have any other shape such as a circular shape, a rectangular shape, a polygonal shape, or a geometric shape. The attaching face 31 may be a recessed cursed surface or a protruding curved surface. For example, the attaching face 31 may be made of a flexible material such as silicon rubber to be deformable.

One face of the double-sided tape 26 is attached to, for example, the attaching face 31. The other face of the double-sided tape 26 is attached to, for example, the chest of the user. As a result, the attaching face 31 is attached to the chest of the user through the double-sided tape 26. The chest of the user is an example of a detection target. The attaching face 31 may be attached to any other portion. For example, the attaching face 31 may be attached to any other portion of the user such as an arm. When the detection target is an object such as wood or metal, the attaching face 31 may be attached to the object.

The attaching face 31 may be attached to the chest of the user through any other means rather than the double-sided tape 26. For example, the attaching face 31 may be made of silicon gel so that the attaching face 31 is attached directly to the chest of the user.

As described above, the attaching face 31 is attached to the chest of the user. In other words, the attaching face 31 is held in a state in which it comes into contact with the chest of the user directly or through the member such as the double-sided tape 26. However, the attaching face 31 need not be fixed to the chest of the user through an adhesive and bonding means. For example, the attaching face 31 may be held in a state in which it comes into contact with the chest of the user such that any other portion of the housing 21 is fixed to the user. For example, the attaching face 31 may be held in a state in which it comes into contact with the chest of the user such that the housing 21 is attached to the body of the user through a belt.

The first positive electrode 22, the second positive electrode 23, the first negative electrode 24, and the second negative electrode 25 are electrodes used to detect the heart rate of the user. Each of the first positive electrode 22, the second positive electrode 23, the first negative electrode 24, and the second negative electrode 25 is provided on the attaching face 31. Some of the first positive electrode 22, the second positive electrode 23, the first negative electrode 24, and the second negative electrode 25 may be provided at any other position.

The first positive electrode 22, the second positive electrode 23, the first negative electrode 24, and the second negative electrode 25 are arranged side by side in a direction in which the attaching face 31 is extended. The arrangement of the first positive electrode 22, the second positive electrode 23, the first negative electrode 24, and the second negative electrode 25 is not limited to this example.

The first positive electrode 22 is closer to an edge 31a of the attaching face 31 than the first negative electrode 24. The second positive electrode 23 is farther from the edge 31a of the attaching face 31 than the second negative electrode 25. The second positive electrode 23 and the first negative electrode 24 are arranged between the first positive electrode 22 and the second negative electrode 25. In other words, the first positive electrode 22 and the second negative electrode 25 are arranged at both ends of the first positive electrode 22, the second positive electrode 23, the first negative electrode 24, and the second negative electrode 25 that are lined up.

The double-sided tape 26 is provided with four holes 34. Each of the holes 34 is larger than each of the first positive electrode 22, the second positive electrode 23, the first negative electrode 24, and the second negative electrode 25. The four holes 34 expose the first positive electrode 22, the second positive electrode 23, the first negative electrode 24, and the second negative electrode 25. Thus, when the attaching face 31 is attached to the chest of the user through the double-sided tape 26, the first positive electrode 22, the second positive electrode 23, the first negative electrode 24, and the second negative electrode 25 can come into contact with the chest of the user.

Figure 3:
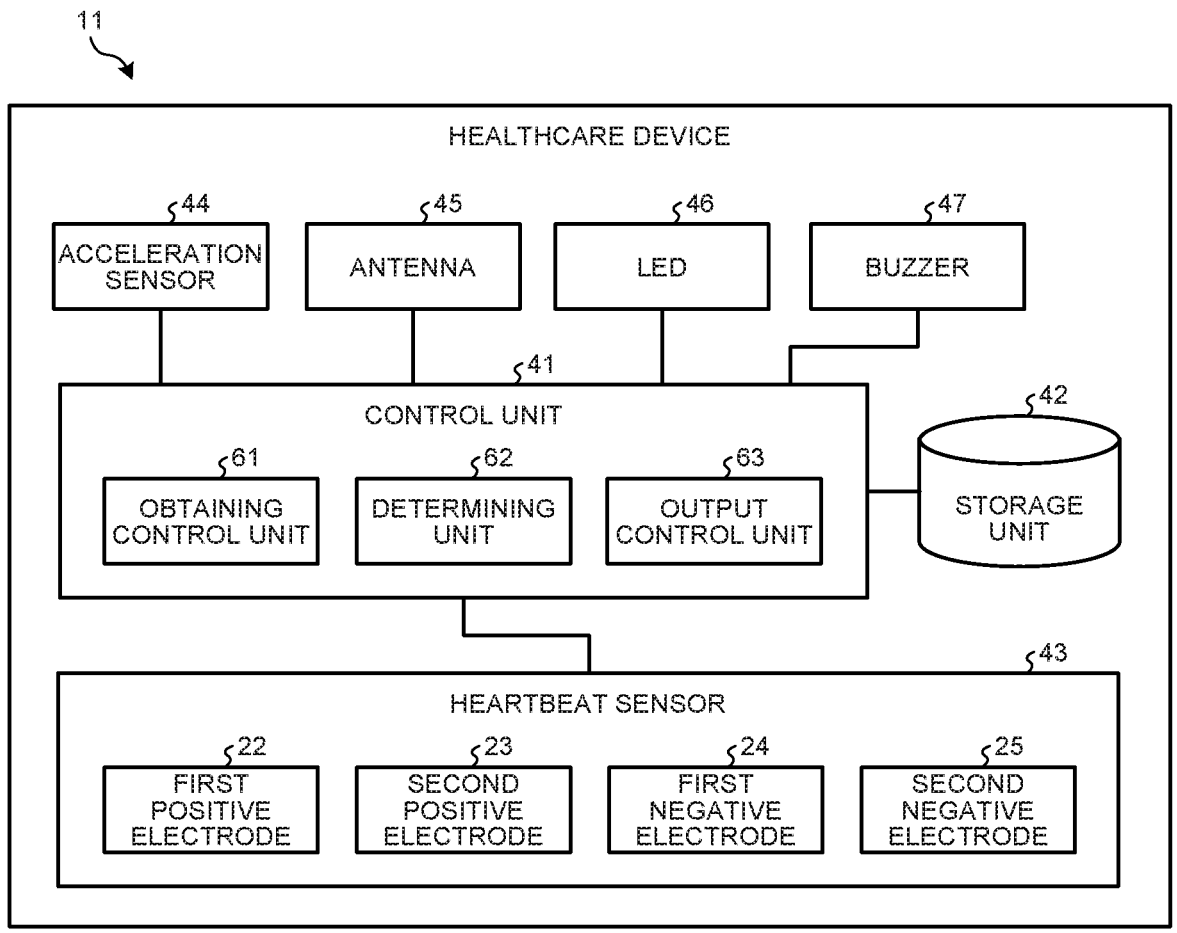
FIG. 3 is a block diagram illustrating an exemplary configuration of the healthcare device according to the first embodiment.

FIG. 3 is a block diagram illustrating an exemplary configuration of the healthcare device 11 according to the first embodiment. The healthcare device 11 includes a control unit 41, a storage unit 42, a heartbeat sensor 43, an acceleration sensor 44, an antenna 45, a light-emitting diode (LED) 46, and a buzzer 47 as illustrated in FIG. 3.

The control unit 41 can also be referred to as, for example, a control device or a control circuit. The heartbeat sensor 43 is an example of a sensing circuit, and can also be referred to as, for example, a detecting unit, a finding unit, an observing unit, a sensor, a part, or a portion. A circuit may be made of a single component, or may be provided on a substrate, including a component or components and a wiring or wirings, for example. The circuit may implement a functional configuration or configurations through a collaboration with a program, for example. Each of the antenna 45, the LED 46, and the buzzer 47 is an example of first to fourth output units. Each of the first to fourth output units may be made of a single component, or may be a circuit provided on a substrate, including a component or components and a wiring or wirings, for example. Each of the first to fourth output units may implement a functional configuration or configurations through a collaboration with a program, for example. The antenna 45 is an example of a receiving component and can also be referred to as, for example, a transmitting unit, a communication unit, a part, or a portion. The LED 46 is an example of a light emitting component and can also be referred to as, for example, a light source, a display unit, a part, or a portion. The buzzer 47 is an example of a sounding component and can also be referred to as, for example, a sound source, a sound emitting unit, a part, or a portion.

The control unit 41 controls various operations in the healthcare device 11 in general. For example, the control unit 41 is a microprocessor equipped with a central processing unit (CPU) therein. The control unit 41 is not limited to this example and may be any other device. For example, each of the functions of the control unit 41 may be implemented by each of portions or a collaboration of a plurality of portions distributed in a circuit including various electronic parts.

The storage unit 42 stores information that is used by the control unit 41. For example, the storage unit 42 includes a read only memory (ROM) that stores a control program executed by the CPU with which the control unit 41 is equipped therein, a random access memory (RAM) that provides a work area to the CPU, and a non-volatile memory that stores various kinds of information.

The heartbeat sensor 43 includes the first positive electrode 22, the second positive electrode 23, the first negative electrode 24, and the second negative electrode 25 described above. For example, the heartbeat sensor 43 obtains an action potential (hereinafter, referred to as a "heart action potential") of the heart of the user from the first positive electrode 22, the second positive electrode 23, the first negative electrode 24, and the second negative electrode 25 in the chest of the user. The heart action potential is an example of biological information and first biological information of the detection target. As described above, an interface such as the first positive electrode 22, the second positive electrode 23, the first negative electrode 24, or the second negative electrode 25 may be a portion or a component with which an element such as the heartbeat sensor 43 can sense or detect a physical property. The action potential refers to a change in electrical potential associated with the passage of an impulse along the membrane of a muscle cell or nerve cell.

Figure 4:
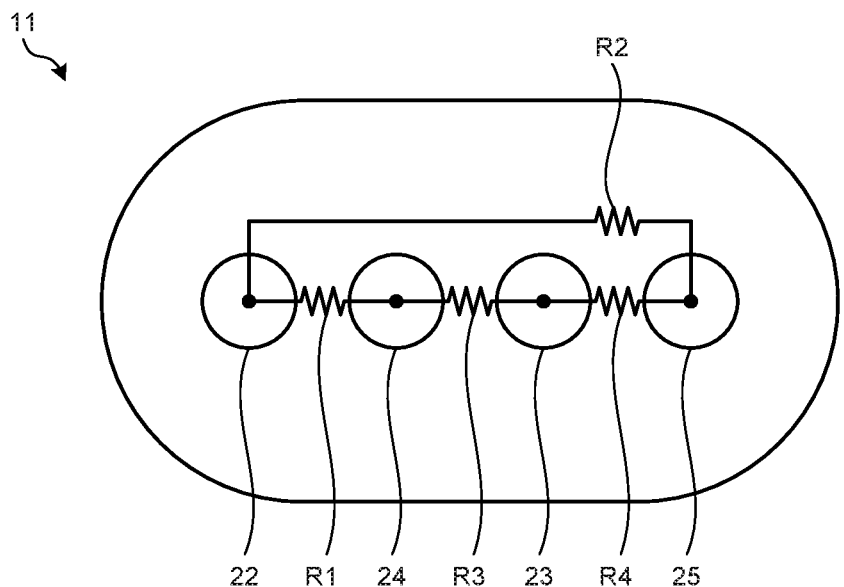
FIG. 4 is a plane view schematically illustrating an electric pathway among electrodes according to the first embodiment.
Figure 5:
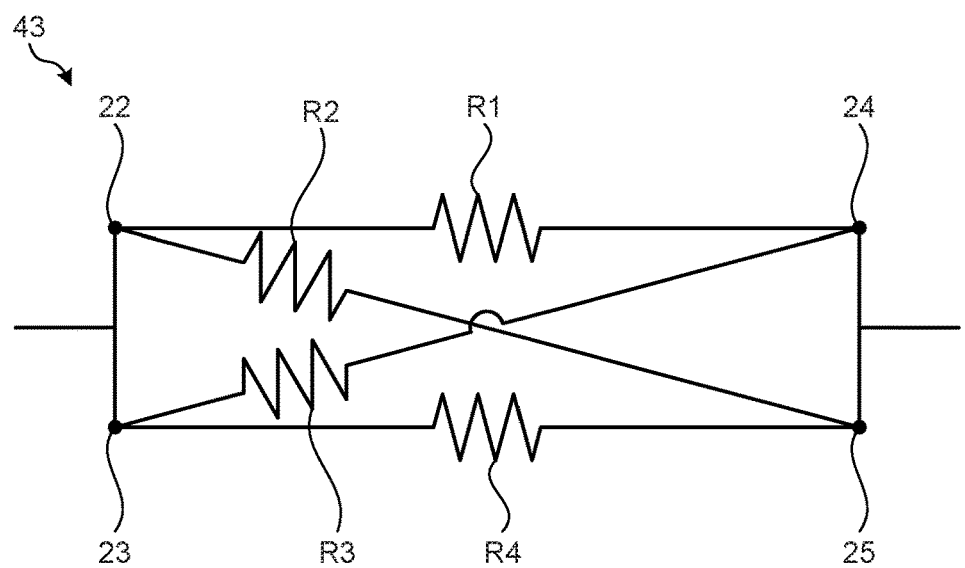
FIG. 5 is a circuit diagram schematically illustrating a part of a circuit of a heartbeat sensor according to the first embodiment.

FIG. 4 is a plane view schematically illustrating an electric pathway among the electrodes 22 to 25 according to the first embodiment. FIG. 5 is a circuit diagram schematically illustrating a part of a circuit of the heartbeat sensor 43 according to the first embodiment. The first positive electrode 22, the second positive electrode 23, the first negative electrode 24, and the second negative electrode 25 come into contact with the chest of the user and are thus electrically connected with one another via the chest (the body surface) of the user as illustrated in FIG. 4 and FIG. 5.

For example, on the chest (the body surface) of the user, electricity flows between the first positive electrode 22 and the first negative electrode 24. In other words, an electric pathway is formed between the first positive electrode 22 and the first negative electrode 24 through the body surface of the user as illustrated in FIG. 4. In the present embodiment, a resistance value between the first positive electrode 22 and the first negative electrode 24 is indicated by R1.

On the body surface of the user, electricity flows between the first positive electrode 22 and the second negative electrode 25. In other words, an electric pathway is formed between the first positive electrode 22 and the second negative electrode 25 through the body surface of the user. In the present embodiment, a resistance value between the first positive electrode 22 and the second negative electrode 25 is indicated by R2.

On the body surface of the user, electricity flows between the second positive electrode 23 and the first negative electrode 24. In other words, an electric pathway is formed between the second positive electrode 23 and the first negative electrode 24 through the body surface of the user. In the present embodiment, a resistance value between the second positive electrode 23 and the first negative electrode 24 is indicated by R3.

On the body surface of the user, electricity flows between the second positive electrode 23 and the second negative electrode 25. In other words, an electric pathway is formed between the second positive electrode 23 and the second negative electrode 25 through the body surface of the user. In the present embodiment, a resistance value between the second positive electrode 23 and the second negative electrode 25 is indicated by R4.

As described above, the first negative electrode 24 is connected to the first positive electrode 22 and the second positive electrode 23 through the body surface of the user. In other words, the first negative electrode 24 is connected to the first positive electrode 22 and the second positive electrode 23 in parallel through the body surface of the user.

The second negative electrode 25 is connected to the first positive electrode 22 and the second positive electrode 23 through the body surface of the user. In other words, the second negative electrode 25 is connected to the first positive electrode 22 and the second positive electrode 23 in parallel through the body surface of the user.

The heartbeat sensor 43 obtains the heart action potentials and the resistance values R1 to R4 of the body surface of the user from the first positive electrode 22, the second positive electrode 23, the first negative electrode 24, and the second negative electrode 25. In other words, the heartbeat sensor 43 senses or detects the heart action potentials and the resistance values R1 to R4 of the body surface of the user with the first positive electrode 22, the second positive electrode 23, the first negative electrode 24, and the second negative electrode 25. For example, the heartbeat sensor 43 obtains the heart action potentials and the resistance values R1 to R4, for example, through a four-terminal sensing. The heartbeat sensor 43 outputs information related to the obtained heart action potentials and the resistance values R1 to R4 to the control unit 41.

Figure 6:
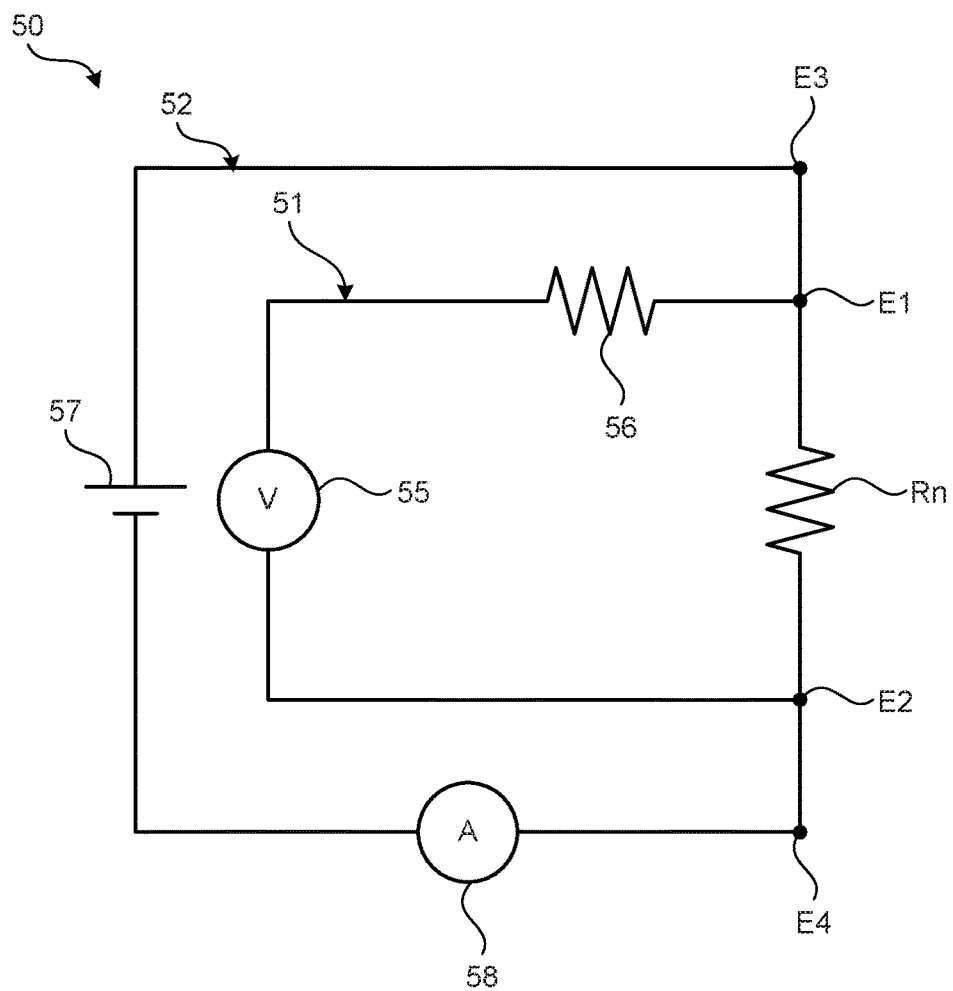
FIG. 6 is a circuit diagram schematically illustrating an example of a measuring unit of the heartbeat sensor according to the first embodiment.

FIG. 6 is a circuit diagram schematically illustrating an example of a measuring unit 50 of the heartbeat sensor 43 according to the first embodiment. An exemplary method of obtaining the heart action potentials and the resistance values through the heartbeat sensor 43 will be described with reference to FIG. 6. The heartbeat sensor 43 includes a plurality of measuring units 50 for obtaining the heart action potentials and the resistance values.

The measuring unit 50 includes a first portion 51 and a second portion 52. The first portion 51 includes a voltmeter 55 and an electric resistor 56 that are connected in series. Terminals E1 and E2 are provided on both ends of the first portion 51. The second portion 52 includes a power source 57 and an ammeter 58 that are connected in series. Terminals E3 and E4 are provided on both ends of the second portion 52.

For example, the four terminals E1 to E4 are electrically connected to a measurement target, and thus the measuring unit 50 can detect an action potential of the measurement target and a resistance value Rn. The four terminals E1 to E4 correspond to the first positive electrode 22, the second positive electrode 23, the first negative electrode 24, and the second negative electrode 25. The resistance value Rn corresponds to each of the resistance values R1 to R4.

The plurality of measuring units 50 described above detects the heart action potentials and the resistance values R1 to R4 between the first positive electrode 22 and the first negative electrode 24, between the first positive electrode 22 and the second negative electrode 25, between the second positive electrode 23 and the first negative electrode 24, and between the second positive electrode 23 and the second negative electrode 25.

For example, the heartbeat sensor 43 includes one measuring unit 50 in which the terminal E1 is the first positive electrode 22, the terminal E2 is the first negative electrode 24, the terminal E3 is the second positive electrode 23, and the terminal E4 is the second negative electrode 25. This measuring unit 50 obtains the heart action potential and the resistance value R1 between the first positive electrode 22 and the first negative electrode 24.

The power source 57 causes a measurement signal current to flow between the second positive electrode 23 (the terminal E3) and the second negative electrode 25 (the terminal E4), and the voltmeter 55 obtains a potential difference (the heart action potential) between the first positive electrode 22 (the terminal E1) and the first negative electrode 24 (the terminal E2). In other words, the voltmeter 55 senses or detects the potential difference between the first positive electrode 22 and the first negative electrode 24. For example, the resistance value R1 (the resistance value Rn) between the first positive electrode 22 and the first negative electrode 24 is obtained based on the potential difference and a current value of the measurement signal current. In other words, the resistance value R1 between the first positive electrode 22 and the first negative electrode 24 is calculated based on the potential difference and a current value of the measurement signal current.

Similarly, the respective measuring units 50 obtain the heart action potentials and the resistance values R2 to R4 between the first positive electrode 22 and the second negative electrode 25, between the second positive electrode 23 and the first negative electrode 24, and between the second positive electrode 23 and the second negative electrode 25.

In the present embodiment, the resistance values of the electric resistors 56 of the measuring units 50 differ from one another. When the electric resistor 56 is not provided in the measuring unit 50, the resistance values R1 to R4 are almost equal. However, the electric resistors 56 having the different resistance values are provided in the respective measuring units 50, the resistance values R1 to R4 differ from one another. The electric resistor 56 may not be provided in the measuring unit 50.

The present embodiment is not limited to the four-terminal sensing, and the heart action potentials and the resistance values R1 to R4 between the first positive electrode 22 and the first negative electrode 24, between the first positive electrode 22 and the second negative electrode 25, between the second positive electrode 23 and the first negative electrode 24, and between the second positive electrode 23 and the second negative electrode 25 may be obtained through another method such as a two-terminal sensing.

The acceleration sensor 44 illustrated in FIG. 3 is accommodated in the housing 21. The acceleration sensor 44 detects acceleration of the healthcare device 11. The acceleration sensor 44 outputs the detected acceleration to the control unit 41.

The antenna 45 is accommodated in the housing 21. The antenna 45 is an antenna for performing wireless communication, for example, via wireless network such as a wireless LAN, the Bluetooth, or a 3G network. The healthcare device 11 may include a plurality of types of antennas 45.

The LED 46 is accommodated in the housing 21. The LED 46 is controlled by the control unit 41 and emits light toward the outside of the housing 21. For example, the LED 46 is turned on, blinks, or turned off. The healthcare device 11 may include a plurality of types of LEDs 46.

The buzzer 47 is accommodated in the housing 21. The buzzer 47 is controlled by the control unit 41 and emits a sound. The healthcare device 11 may include any other part that emits a sound such as a speaker instead of the buzzer 47.

The control unit 41 implements an obtaining control unit 61, a determining unit 62, and an output control unit 63, for example, through a collaboration with a program stored in the storage unit 42 as illustrated in FIG. 3. The control unit 41 may implement any other functional configuration. Each of the obtaining control unit 61, the determining unit 62, and the output control unit 63 may be configured of hardware or software alone.

The obtaining control unit 61 obtains the heart action potentials and the resistance values R1 to R4 from the heartbeat sensor 43. In other words, the obtaining control unit 61 receives the heart action potentials and resistance values R1 to R4 from the heartbeat sensor 43. The obtaining control unit 61 generates an electrocardiogram based on the obtained heart action potential. The obtaining control unit 61 calculates the heart rate of the user from the generated electrocardiogram. The obtaining control unit 61 outputs, for example, information related to the electrocardiogram and the heart rate to the output control unit 63.

The obtaining control unit 61 calculates a resistance value R between the first and second positive electrodes 22 and 23 and the first and second negative electrodes 24 and 25 from the resistance values R1 to R4. The calculated resistance value R is expressed by the following Formula (1):

$$R = (R1 \times R2 \times R3 \times R4)/(R1+R2+R3+R4) \quad (1)$$

The obtaining control unit 61 outputs information related to the heart action potentials and the resistance values R, R1, R2, R3, and R4 to the determining unit 62.

Figure 7:
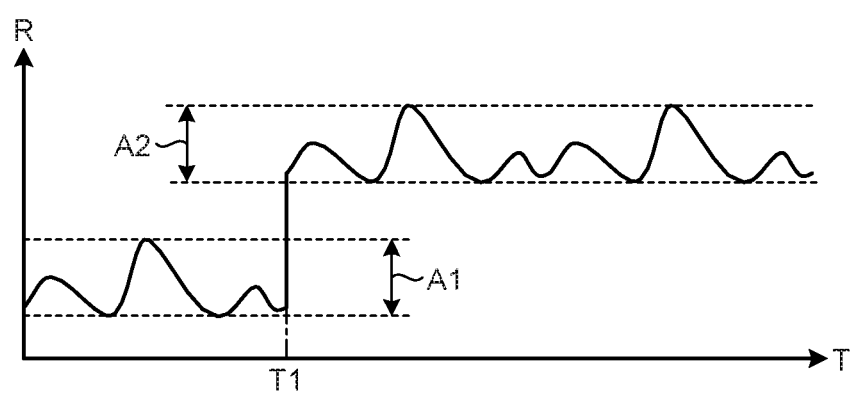
FIG. 7 is a graph illustrating an example of a resistance value according to the first embodiment.

FIG. 7 is a graph illustrating an example of the resistance value R according to the first embodiment. In FIG. 7, a vertical axis indicates the resistance value R, and a horizontal axis indicates a time T. The resistance value R between the first and second positive electrodes 22 and 23 and the first and second negative electrodes 24 and 25 has, for example, a waveform illustrated in FIG. 7. FIG. 7 illustrates an example in which the first positive electrode 22 is separated from the chest of the user at a separation time T1.

When the first positive electrode 22 is separated from the chest of the user, the resistance value R1 between the first positive electrode 22 and the first negative electrode 24 is substantially infinite. Further, the resistance value R2 between the first positive electrode 22 and the second negative electrode 25 is substantially infinite.

In the above state, even when the first positive electrode 22 is separated from the chest of the user, the second positive electrode 23, the first negative electrode 24, and the second negative electrode 25 continuously come into contact with the chest of the user. Thus, the resistance value R3 between the second positive electrode 23 and the first negative electrode 24 and the resistance value R4 between the second positive electrode 23 and the second negative electrode 25 do not change significantly.

As described above, when the first positive electrode 22 is separated from the chest of the user, the resistance values R1 and R2 are substantially infinite, but the resistance values R3 and R4 do not change significantly. Thus, through Formula (1), the resistance value R increases but does not become infinite. The resistance value R increases after the separation time T1 at which the first positive electrode 22 is separated from the chest of the user as illustrated in FIG. 7.

An amplitude A1 of the resistance value R before the separation time T1 is substantially the same as an amplitude A2 of the resistance value R after the separation time T1. The amplitudes A1 and A2 are a maximum displacement of the waveform of the resistance value R. As described above, when the first positive electrode 22 is separated from the chest of the user, the resistance value R is shifted in a state in which almost the same waveform is maintained. After the first positive electrode 22 is separated from the chest of the user, the waveform of the resistance value R may change.

When the first positive electrode 22 is separated from the chest of the user, since the resistance values R1 and R2 become infinite, the potential difference between the first positive electrode 22 and the first negative electrode 24 becomes 0 V. Similarly, the potential difference between the first positive electrode 22 and the second negative electrode 25 becomes 0 V. However, the potential difference between the second positive electrode 23 and the first negative electrode 24 does not decrease significantly. Similarly, the potential difference between the second positive electrode 23 and the second negative electrode 25 does not decrease significantly. Thus, the heartbeat sensor 43 can continuously obtain the heart action potential and the resistance values R3 and R4 from the second positive electrode 23, the first negative electrode 24, and the second negative electrode 25.

The above description has been made in connection with the example in which the first positive electrode 22 is separated from the chest of the user. However, the same applies even when any one of the second positive electrode 23, the first negative electrode 24, and the second negative electrode 25 is separated from the chest of the user, and the same applies even when either of the first positive electrode 22 and the second positive electrode 23 and either of the first negative electrode 24 and the second negative electrode 25 are separated from the chest of the user. In other words, when any one of the first positive electrode 22, the second positive electrode 23, the first negative electrode 24, and the second negative electrode 25 or one of the first positive electrode 22 and the second positive electrode 23 and one of the first negative electrode 24 and the second negative electrode 25 are separated from the chest of the user, and the others of the first positive electrode 22, the second positive electrode 23, the first negative electrode 24, and the second negative electrode 25 or the other one of the first positive electrode 22 and the second positive electrode 23 and the other one of the first negative electrode 24 and the second negative electrode 25 come into contact with the chest of the user, the resistance value R increases.

The determining unit 62 determines whether or not it is a state (hereinafter, referred to as a "partially peeled state") in which any one of the first positive electrode 22, the second positive electrode 23, the first negative electrode 24, and the second negative electrode 25 or one of the first positive electrode 22 and the second positive electrode 23 and one of the first negative electrode 24 and the second negative electrode 25 are separated from the chest of the user, and the others of the first positive electrode 22, the second positive electrode 23, the first negative electrode 24, and the second negative electrode 25 or the other one of the first positive electrode 22 and the second positive electrode 23 and the other one of the first negative electrode 24 and the second negative electrode 25 come into contact with the chest of the user.

For example, the determining unit 62 determines that it is the partially peeled state when one to three of the four resistance values R1 to R4 are substantially infinite. For example, when each of the resistance values R1 to R4 exceeds a threshold value stored in the storage unit 42 in advance, the determining unit 62 determines that each of the resistance values R1 to R4 is substantially infinite. In other words, the determining unit 62 determines whether or not it is the partially peeled state based on an increase in the resistance values R1 to R4 of the body surface of the user between the first positive electrode 22 and the second positive electrode 23 and the first negative electrode 24 and the second negative electrode 25. As described above, the resistance values R1 to R4 are obtained based on the current value of the measurement signal current. Thus, according to another expression, when one to three of the current values of the measurement signal currents flowing between the first positive electrode 22 and the second positive electrode 23 and the first negative electrode 24 and the second negative electrode 25 is smaller than a predetermined value, the determining unit 62 determines that it is the partially peeled state.

When all of the first positive electrode 22, the second positive electrode 23, the first negative electrode 24, and the second negative electrode 25 are separated from the chest of the user, all the resistance values R1 to R4 are substantially infinite. Thus, the resistance value R becomes infinite as well. Similarly, for example, there are cases in which the resistance value R is infinite when an abnormality occurs in the user.

When all the resistance values R1 to R4 are infinite, the determining unit 62 determines whether it is a state (hereinafter, referred to as a "completely peeled state") in which all the first positive electrode 22, the second positive electrode 23, the first negative electrode 24, and the second negative electrode 25 are separated from the chest of the user, or an abnormality occurs in the user. For example, the determining unit 62 determines that it is the completely peeled state when it is determined to be the partially peeled state in advance, and all the resistance values R1 to R4 are substantially infinite. According to another expression, when all of the current values of the measurement signal current flowing among the first positive electrode 22, the second positive electrode 23, the first negative electrode 24, and the second negative electrode 25 are smaller than a predetermined value, the determining unit 62 determines that it is the completely peeled state. On the other hand, the determining unit 62 determines that an abnormality occurs in the user when it is determined to be not the partially peeled state, and all the resistance values R1 to R4 are substantially infinite.

The output control unit 63 controls, for example, the antenna 45 such that the information related to the electrocardiogram and the heart rate obtained from the obtaining control unit 61 is transmitted to the first server 13. The first server 13 transmits the received information related to the electrocardiogram and the heart rate to the information terminal 12 of the observer. The information terminal 12 displays the received information related to the electrocardiogram and the heart rate through the display unit 12a. As a result, the observer can understand the information related to the electrocardiogram and the heart rate of the user.

The output control unit 63 obtains the determination result from the determining unit 62. In other words, the output control unit 63 receives the determination result from the determining unit 62. For example, when the determining unit 62 determines that it is the partially peeled state or the completely peeled state, the output control unit 63 controls the antenna 45 such that the determination result is transmitted to the first server 13. Similarly, when the determining unit 62 determines that an abnormality occurs in the user, the output control unit 63 controls the antenna 45 such that the determination result is transmitted to the first server 13. In other words, the antenna 45 outputs information to the first server 13 when it is the partially peeled state or the completely peeled state, or an abnormality occurs in the user.

The first server 13 transmits information related to the received determination result to the information terminal 12 of the observer. The information terminal 12 displays the information related to the received determination result through the display unit 12a. As a result, the observer can understand peeling of the healthcare device 11 and the abnormality in the user.

Further, when the determining unit 62 determines that it is the partially peeled state or the completely peeled state, or an abnormality occurs in the user, the output control unit 63 controls the LED 46 such that the LED 46 emits light. As the LED 46 emits light, the user or a person around the user is notified of the partially peeled state, the completely peeled state, or the occurrence of the abnormality in the user. For example, the LED 46 blinks in the partially peeled state and is turned on when an abnormality occurs in the user. As the LED 46 emits light when it is the partially peeled state or the completely peeled state or when an abnormality occurs in the user, LED 46 sends out information for notifying of the contact state of the healthcare device 11 or the health state of the user.

Further, when the determining unit 62 determines that it is the partially peeled state or the completely peeled state or when an abnormality occurs in the user, the output control unit 63 controls the buzzer 47 such that a sound is emitted from the buzzer 47. As the buzzer 47 emits a sound, the user or a person around the user is notified of the partially peeled state, the completely peeled state, or the occurrence of the abnormality in the user. For example, the buzzer 47 emits a short small sound in the partially peeled state and emits a long large sound when an abnormality occurs in the user. As described above, the buzzer 47 sends out the information for notifying the contact state of the healthcare device 11 or the health state of the user by emitting a sound through the buzzer 47 when it is the partially peeled state or the completely peeled state or when the user is abnormal.

Figure 8:
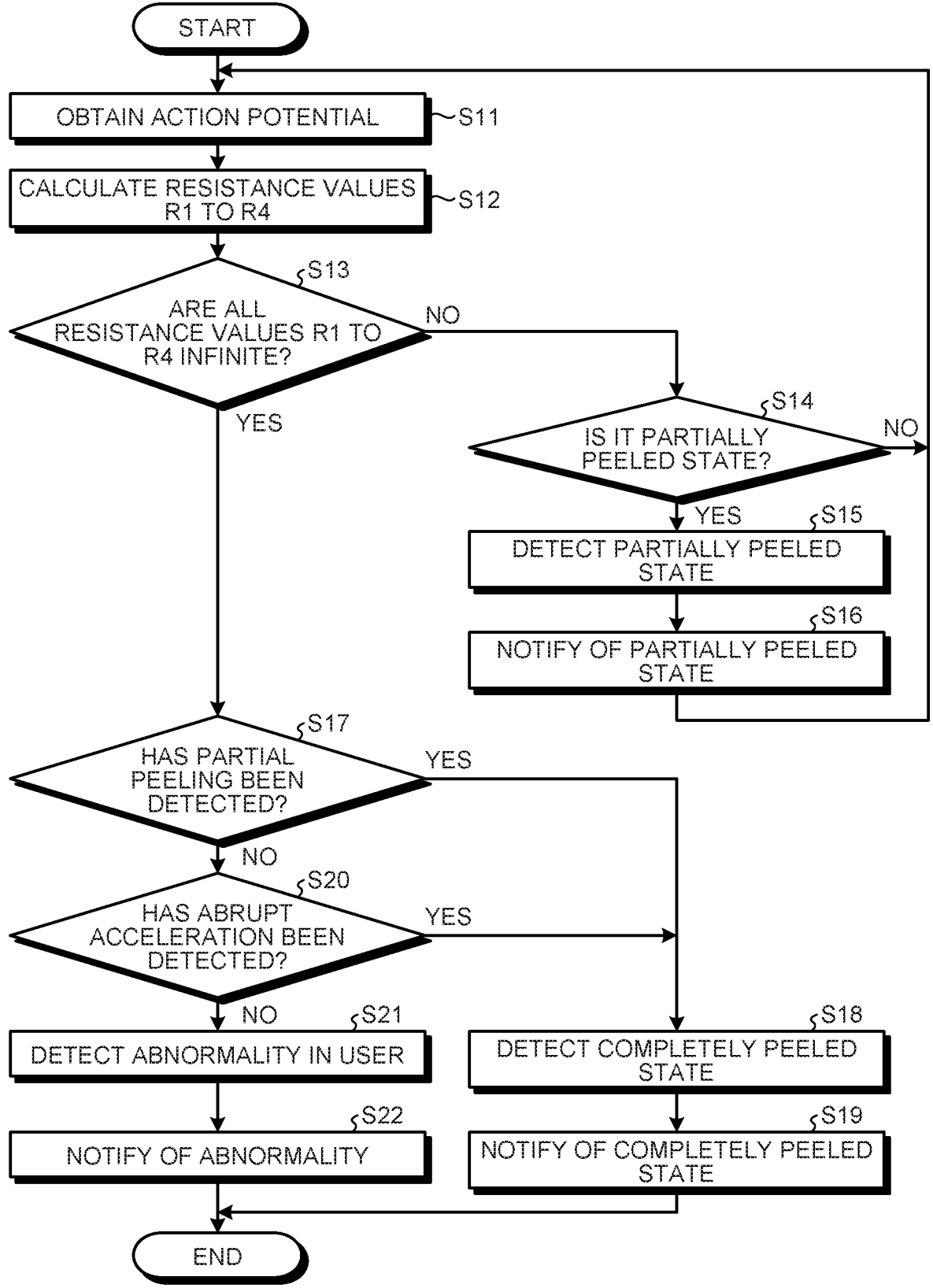
FIG. 8 is a flowchart illustrating a part of an abnormality detection process performed by the healthcare device according to the first embodiment.

FIG. 8 is a flowchart illustrating a part of an abnormality detection process performed by the healthcare device 11 according to the first embodiment. An example of the abnormality detection process executed by the healthcare device 11 will be described below with reference to the flowchart of FIG. 8.

First, the obtaining control unit 61 obtains the heart action potential of the user from the heartbeat sensor 43 (S11). The obtaining control unit 61 obtains the heart action potentials between the first positive electrode 22 and the first negative electrode 24, between the first positive electrode 22 and the second negative electrode 25, between the second positive electrode 23 and the first negative electrode 24, and between the second positive electrode 23 and the second negative electrode 25 from the heartbeat sensor 43. The obtaining control unit 61 generates four electrocardiograms and calculates four heart rates from, for example, the four obtained heart action potentials. Then, the obtaining control unit 61 calculates the resistance values R1 to R4 from the heart action potentials (S12).

Then, the determining unit 62 determines whether or not all the resistance values R1 to R4 are substantially infinite (S13). As described above, the determining unit 62 determines that the resistance values R1 to R4 are substantially infinite, for example, when the resistance values R1 to R4 exceed a previously set threshold value.

When any one of the resistance values R1 to R4 is not substantially infinite (S13: No), the determining unit 62 determines whether or not it is the partially peeled state (S14). For example, the determining unit 62 determines whether or not one to three of the resistance values R1 to R4 are substantially infinite.

When one to three of the resistance values R1 to R4 are substantially infinite (S14: Yes), the determining unit 62 detects the partially peeled state (S15). For example, the output control unit 63 notifies the user and the observer of that it is the partially peeled state (S16). For example, the output control unit 63 controls the antenna 45 such that information indicating that it is the partially peeled state is transmitted to the information terminal 12 of the observer through the first server 13. Further, the output control unit 63 controls the LED 46 and the buzzer 47 such that the user is notified of that it is the partially peeled state through light and a sound.

When the user and the observer is notified of that it is the partially peeled state, the obtaining control unit 61 obtains the heart action potential again (S11). Similarly, when all of the resistance values R1 to R4 is determined to be not substantially infinite in S14 (S14: No), the obtaining control unit 61 obtains the heart action potential again (S11).

When the determining unit 62 determines that all the resistance values R1 to R4 are substantially infinite in S13 (S13: Yes), the determining unit 62 determines whether or not the partial peeling has been detected already (S17). When the partially peeled state has been detected (S17: Yes), the determining unit 62 detects the completely peeled state (S18).

When the completely peeled state is detected, the output control unit 63 notifies, for example, the user and the observer of that it is the completely peeled state (S19). For example, the output control unit 63 controls the antenna 45 such that information indicating that it is the completely peeled state is transmitted to the information terminal 12 of the observer through the first server 13. Further, the output control unit 63 controls the LED 46 and the buzzer 47 such that the user is notified of that it is the completely peeled state through light and a sound. The user who has been notified of that it is the completely peeled state can attach the healthcare device 11 to the chest.

Meanwhile, when the partially peeled state is not detected in S17 (S17: No), the determining unit 62 determines whether or not abrupt acceleration has been detected by the acceleration sensor 44 (S20). For example, when the acceleration detected by the acceleration sensor 44 exceeds a previously set threshold value at a point in time at which all the resistance values R1 to R4 are determined to be infinite, the determining unit 62 determines that the acceleration sensor 44 has detected the abrupt acceleration.

For example, when the user falls down, the first positive electrode 22, the second positive electrode 23, the first negative electrode 24, and the second negative electrode 25 may be separated from the chest of the user at the same time. Thus, when the acceleration sensor 44 detects the abrupt acceleration (S20: Yes), the determining unit 62 detects the completely peeled state (S18). S20 may be omitted.

When the acceleration sensor 44 detects no abrupt acceleration (S20: No), the determining unit 62 detects an abnormality in the user (S21). The output control unit 63 notifies, for example, a person around the user and the observer of the abnormality in the user (S22).

For example, the output control unit 63 controls the antenna 45 such that information related to the occurrence of the abnormality in the user is transmitted to the information terminal 12 of the observer through the first server 13. For example, the observer that has been notified of the abnormality in the user can protect the user by contacting the user or a hospital.

Further, the output control unit 63 controls the LED 46 and the buzzer 47 such that the person around the user is notified of the occurrence of the abnormality in the user through light and a sound. The person around the user who has been notified of the abnormality in the user can protect the user, for example, by performing a life-saving activity for the user or contacting the hospital.

As described above, the healthcare device 11 detects the abnormality in the user and an abnormality in a attaching state (the partially peeled state and the completely peeled state) of the healthcare device 11 based on the resistance values R1 to R4 between the first and second positive electrodes 22 and 23 and the first and second negative electrodes 24 and 25. In other words, the heartbeat sensor 43 of the healthcare device 11 obtains the resistance values R1 to R4 as the information related to the contact state between the first positive electrode 22, the second positive electrode 23, the first negative electrode 24, and the second negative electrode 25 and the chest of the user.

Figure 9:
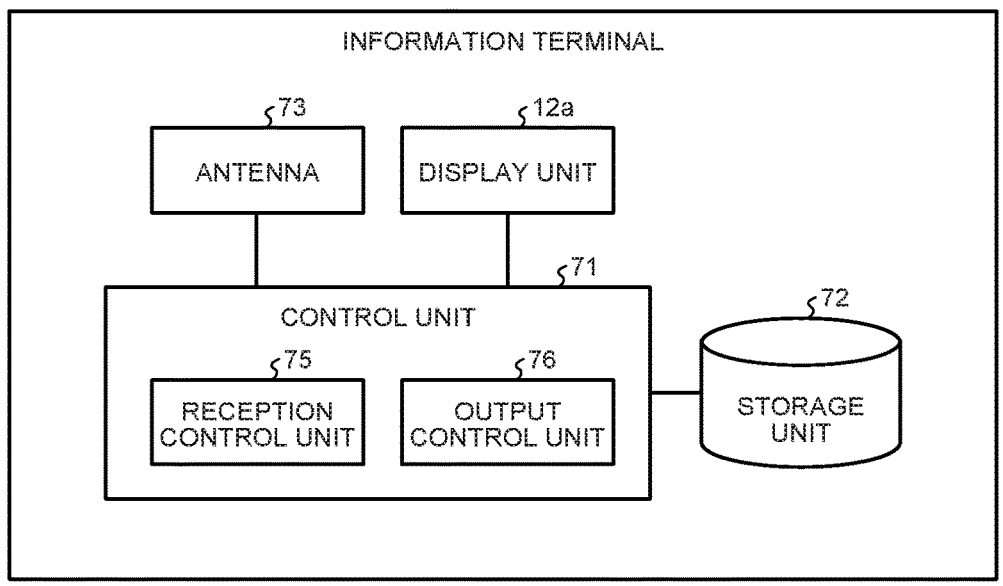
FIG. 9 is a block diagram illustrating an exemplary configuration of an information terminal according to the first embodiment.

FIG. 9 is a block diagram illustrating an exemplary configuration of the information terminal 12 according to the first embodiment. An example of the information terminal 12 according to the first embodiment will be described below in detail with reference to FIG. 9. The information terminal 12 includes a display unit 12a, a control unit 71, a storage unit 72, and an antenna 73 as illustrated in FIG. 9. The control unit 71 can also be referred to as, for example, a control device or a control circuit. The control unit 71 and the antenna 73 can also be referred to as, for example, a receiving component or a sensing circuit.

The control unit 71 controls various kinds of operations in the information terminal 12 in general. The control unit 71 is, for example, a microprocessor equipped with a CPU therein. The control unit 71 is not limited to this example and may be any other device. For example, each of the functions of the control unit 71 may be implemented by each of portions or a collaboration of a plurality of portions distributed in a circuit including various electronic parts. The storage unit 72 stores information that is used by the control unit 71. For example, the storage unit 72 includes a ROM that stores a control program executed by the CPU with which the control unit 71 is equipped therein, a RAM that provides a work area to the CPU, and a non-volatile memory that stores various kinds of information.

The antenna 73 is an antenna for performing wireless communication, for example, via wireless network such as a wireless LAN, the Bluetooth, or a 3G network. The information terminal 12 may include a plurality of types of antennas 73.

The control unit 71 implements a reception control unit 75 and an output control unit 76, for example, through a collaboration with a program stored in the storage unit 72. The control unit 71 may implement any other functional configuration.

The reception control unit 75 obtains the information related to the electrocardiogram and the heart rate of the user obtained by the healthcare device 11 from the signal received by the antenna 73. In other words, the reception control unit 75 receives the information related to the electrocardiogram and the heart rate of the user, from the healthcare device 11. As described above, the controller 71 (the reception control unit 75) receives the information with the antenna 73, and the antenna 73 receives the information from the healthcare device 11 via radio waves. The controller 71 and the antenna 73 may receive the information via wiring, for example. The antenna 73 of the present embodiment receives the signal related to the electrocardiogram and the heart rate of the user from the first server 13 but may receive the information from, for example, the healthcare device 11 or the second server 14.

The reception control unit 75 obtains information related to the determination result of the determining unit 62 of the healthcare device 11 from the signal received by the antenna 73. In other words, when the determining unit 62 determines that it is the partially peeled state or the completely peeled state or an abnormality occurs in the user, the reception control unit 75 obtains information related to the determination result.

The reception control unit 75 outputs the obtained information related to the electrocardiogram and the heart rate of the user and the information related to the determination result to the output control unit 76. The output control unit 76 controls the display unit 12a based on the input information related to the electrocardiogram and the heart rate of the user and the information related to the determination result such that the information is displayed on the display unit 12a.

For example, when it is the state (the partially peeled state) in which any one of the first positive electrode 22, the second positive electrode 23, the first negative electrode 24, and the second negative electrode 25 or one of the first positive electrode 22 and the second positive electrode 23 and one of the first negative electrode 24 and the second negative electrode 25 are separated from the chest of the user, and the others of the first positive electrode 22, the second positive electrode 23, the first negative electrode 24, and the second negative electrode 25, or the other one of the first positive electrode 22 and the second positive electrode 23 and the other one of the first negative electrode 24 and the second negative electrode 25 come into contact with the chest of the user, the output control unit 76 causes text information and image information for notifying of that the healthcare device 11 has entered the partially peeled state to be displayed on the display unit 12a.

Further, when it is in the state (the completely peeled state) in which all of the first positive electrode 22, the second positive electrode 23, the first negative electrode 24, and the second negative electrode 25 are separated from the chest of the user, the output control unit 76 causes text information and image information for notifying of that the healthcare device 11 has entered the completely peeled state to be displayed on the display unit 12a.

The information terminal 12 may include any other part that sends out information such as a speaker or a vibration motor. The output control unit 76 controls the speaker or the vibration motor based on the input information related to the determination result such that information is sent out through a sound or a vibration.

Figure 10:
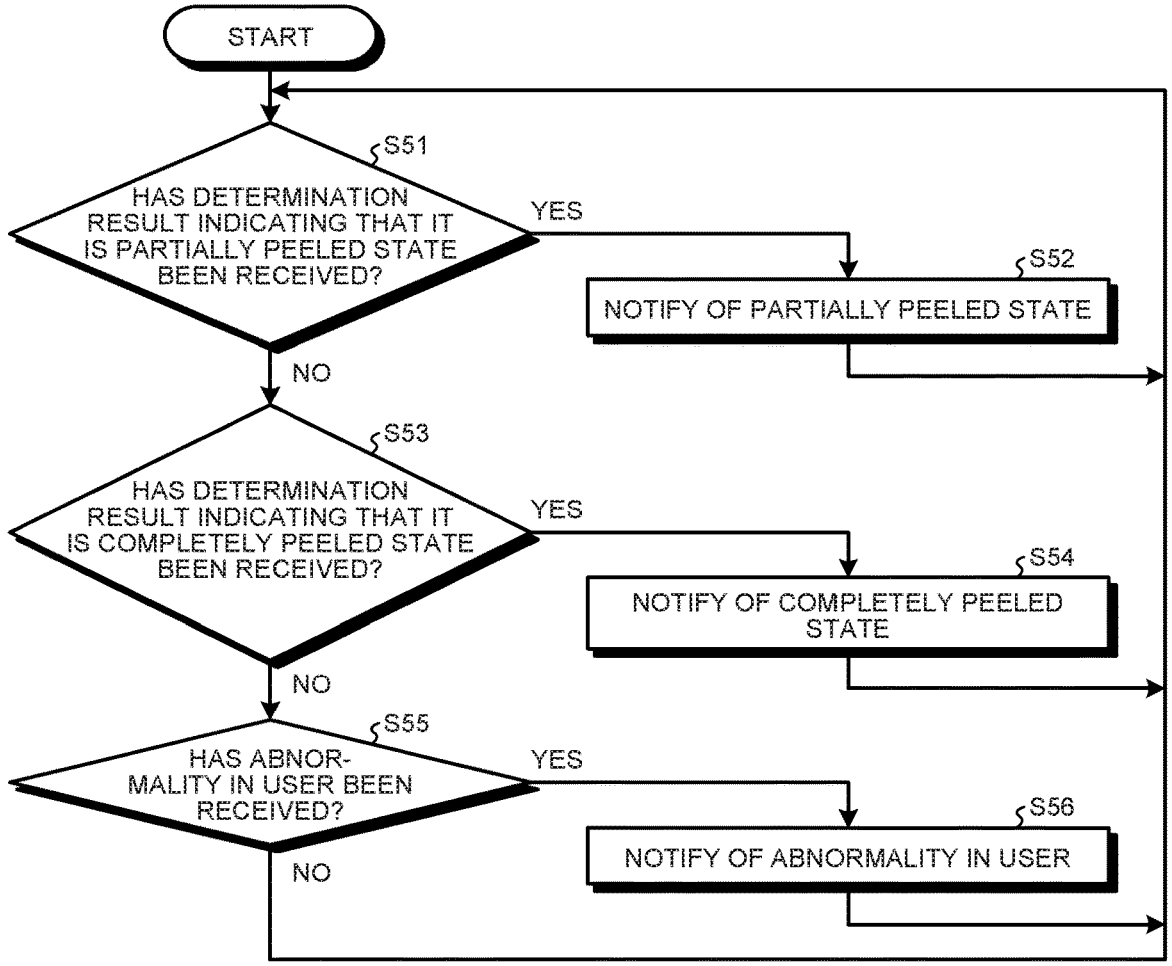
FIG. 10 is a flowchart illustrating a part of a state notification process performed by the information terminal according to the first embodiment.

FIG. 10 is a flowchart illustrating a part of a state notification process performed by the information terminal 12 according to the first embodiment. An example of the state notification process executed by the information terminal 12 will be described below with reference to the flowchart of FIG. 10.

First, the reception control unit 75 determines whether or not the determination result indicating that it is the partially peeled state has been received from the healthcare device 11 (S51). When the reception control unit 75 has received the determination result indicating that it is the partially peeled state (S51: Yes), the output control unit 76 causes, for example, the text information for notifying of that the healthcare device 11 has entered the partially peeled state to be displayed on the display unit 12a, and notifies, for example, the observer of the partially peeled state (S52). When the output control unit 76 causes the information to be displayed on the display unit 12a, the reception control unit 75 returns to the determining as to whether or not the determination result indicating that it is the partially peeled state has been received from the healthcare device 11 (S51).

When the reception control unit 75 has not received the determination result indicating that it is the partially peeled state (S51: No), the reception control unit 75 determines whether or not the determination result indicating that it is the completely peeled state has been received from the healthcare device 11 (S53). When the reception control unit 75 has received the determination result indicating that it is the completely peeled state (S53: Yes), the output control unit 76 causes, for example, the text information for notifying of that the healthcare device 11 has entered the completely peeled state to be displayed on the display unit 12a, and notifies, for example, the observer of the completely peeled state (S54). When the output control unit 76 causes the information to be displayed on the display unit 12a, the reception control unit 75 returns to the determining as to whether or not the determination result indicating that it is the partially peeled state has been received from the healthcare device 11 (S51).

When the reception control unit 75 has not received the determination result indicating that it is the completely peeled state (S53: No), the reception control unit 75 determines whether or not the determination result indicating that an abnormality has occurred in the user has been received from the healthcare device 11 (S55). When the reception control unit 75 has received from the determination result indicating that an abnormality has occurred in the user (S55: Yes), the output control unit 76 causes, for example, the text information for notifying of that an abnormality has occurred in the user to be displayed on the display unit 12a, and notifies, for example, the observer of the abnormality in the user (S56). When the output control unit 76 causes the information to be displayed on the display unit 12a, the reception control unit 75 returns to the determining as to whether or not the determination result indicating that it is the partially peeled state has been received from the healthcare device 11 (S51). When the reception control unit 75 has not received the determination result indicating that an abnormality has occurred in the user (S55: No), the reception control unit 75 returns to the determining as to whether or not the determination result indicating that it is the partially peeled state has been received from the healthcare device 11 (S51).

As described above, the information terminal 12 includes: the antenna 73 configured to receive the information related to the contact state between the first positive electrode 22, the second positive electrode 23, the first negative electrode 24, and the second negative electrode 25 of the healthcare device 11 that obtain the action potential of the body surface of the user and the user; and the display unit 12a configured to output information indicating that it is a state in which at least one of the first positive electrode 22, the second positive electrode 23, the first negative electrode 24, and the second negative electrode 25 is separated from the chest of the user based on the obtained information related to the contact state.

The abnormality detection process described above is performed by only the healthcare device 11. However, the abnormality detection process may be performed by at least one of the healthcare device 11, the information terminal 12, the first server 13, and the second server 14.

For example, after obtaining the heart action potential (S11), the healthcare device 11 may transmit the information related to the heart action potential to the information terminal 12, the first server 13, or the second server 14. In this case, the information terminal 12, the first server 13, or the second server 14 that has received the information may perform S12 to S22. As described above, S12 to S22 in the abnormality detection process may be performed by at least one of the healthcare device 11, the information terminal 12, the first server 13, and the second server 14 or any other device.

In the healthcare device 11 according to the first embodiment, when the healthcare device 11 is peeled from the body surface of the user, during at least a bit of time, at least one of the first positive electrode 22, the second positive electrode 23, the first negative electrode 24, and the second negative electrode 25 is separated from the body surface of the user, and the other or others of the first positive electrode 22, the second positive electrode 23, the first negative electrode 24, and the second negative electrode 25 are brought into contact with the body surface of the user. The heartbeat sensor 43 detects the heart action potentials serving as the biological information of the user and the resistance values R1 to R4 with the plurality of electrodes 22 to 25. The antenna 45, the LED 46, and the buzzer 47 send out information when at least one of the first positive electrode 22, the second positive electrode 23, the first negative electrode 24, and the second negative electrode 25 is separated from the body surface of the user, and the other or others of the first positive electrode 22, the second positive electrode 23, the first negative electrode 24, and the second negative electrode 25 are brought into contact with the body surface of the user. As a result, the user and/or the observer can notice that the healthcare device 11 has been peeled off from the body surface of the user in real time or later based on the information sent out by the antenna 45, the LED 46, and the buzzer 47. Thus, the user and/or the observer can distinguish that the healthcare device 11 has been peeled off from the body surface of the user and that an abnormality has occurred in the user.

In other words, the heartbeat sensor 43 detects at least one type of biological information of the user with the first positive electrode 22, the second positive electrode 23, the first negative electrode 24, and the second negative electrode 25. When the healthcare device 11 is peeled off from the body surface of the user, during at least a bit of time, at least one of the first positive electrode 22, the second positive electrode 23, the first negative electrode 24, and the second negative electrode 25 is separated from the body surface of the user, and the other or others of the first positive electrode 22, the second positive electrode 23, the first negative electrode 24, and the second negative electrode 25 are brought into contact with the body surface of the user. In this case, the biological information detected with the first positive electrode 22, the second positive electrode 23, the first negative electrode 24, or the second negative electrode 25 that is separated from the body surface of the user is abnormal, but the biological information detected with the first positive electrode 22, the second positive electrode 23, the first negative electrode 24, or the second negative electrode 25 that is brought into contact with the body surface of the user is normal. As a result, it can be understood that the healthcare device 11 has been peeled off from the body surface of the user in real time or later based on at least one type of biological information detected with a plurality of electrodes, that is, the first positive electrode 22, the second positive electrode 23, the first negative electrode 24, and the second negative electrode 25. Thus, it is possible to distinguish that the healthcare device 11 has been peeled off from the body surface of the user and that an abnormality has occurred in the user.

Further, according to another expression, the heartbeat sensor 43 obtains the information related to the contact state between the first positive electrode 22, the second positive electrode 23, the first negative electrode 24, and the second negative electrode 25 and the body surface of the user from the first positive electrode 22, the second positive electrode 23, the first negative electrode 24, and the second negative electrode 25. As a result, an abnormality in the contact state between the first positive electrode 22, the second positive electrode 23, the first negative electrode 24, and the second negative electrode 25 and the body surface of the user can be understood in real time or later based on the information related to the contact state. Thus, it is possible to distinguish that the healthcare device 11 has been peeled off from the body surface of the user and that an abnormality has occurred in the user.

The heartbeat sensor 43 includes a plurality of electrodes including the first positive electrode 22, the second positive electrode 23, the first negative electrode 24, and the second negative electrode 25. When any one of the first positive electrode 22, the second positive electrode 23, the first negative electrode 24, and the second negative electrode 25 is separated from the body surface of the user, a corresponding one of the resistance values R1 to R4 becomes substantially infinite. Thus, it is possible to easily detect that each of the first positive electrode 22, the second positive electrode 23, the first negative electrode 24, and the second negative electrode 25 is separated from the body surface of the user.

The first negative electrode 24 is connected to the first positive electrode 22 and the second positive electrode 23 via the body surface of the user in parallel, and the second negative electrode 25 is connected to the first positive electrode 22 and the second positive electrode 23 via the body surface of the user in parallel. As a result, when at least one of the first positive electrode 22 and the second positive electrode 23 and at least one of the first negative electrode 24 and the second negative electrode 25 is brought into contact with the body surface of the user, the heartbeat sensor 43 can detect the biological information. Thus, even when any one of the first positive electrode 22, the second positive electrode 23, the first negative electrode 24, and the second negative electrode 25 or one of the first positive electrode 22 and the second positive electrode 23 and one of the first negative electrode 24 and the second negative electrode 25 are separated from the body surface of the user, the heartbeat sensor 43 can continuously detect the biological information, and thus reliability of the biological information detected by the heartbeat sensor 43 is further improved.

The heartbeat sensor 43 detects the action potential of the user with the first positive electrode 22, the second positive electrode 23, the first negative electrode 24, and the second negative electrode 25. It is further beneficial if the user can distinguish that the healthcare device 11 has been peeled off from the body surface of the user and that an abnormality has occurred in the body surface of the user when the heartbeat sensor 43 detects the heart action potential as described above. For example, a possibility that the user will misunderstand the situation in which the healthcare device 11 has been peeled off from the body surface of the user as the abnormality in the user such as a cardiopulmonary arrest is reduced.

The determining unit 62 determines whether or not it is the state in which any one of the first positive electrode 22, the second positive electrode 23, the first negative electrode 24, and the second negative electrode 25 or one of the first positive electrode 22 and the second positive electrode 23 and one of the first negative electrode 24 and the second negative electrode 25 are separated from the body surface of the user, and the others of the first positive electrode 22, the second positive electrode 23, the first negative electrode 24, and the second negative electrode 25 or the other one of the first positive electrode 22 and the second positive electrode 23 and the other one of the first negative electrode 24 and the second negative electrode 25 are brought into contact with the body surface of the user based on an increase in the resistance values R1 to R4 between each of the first positive electrode 22 and the second positive electrode 23 and each of the first negative electrode 24 and the second negative electrode 25.

When any one of the first positive electrode 22, the second positive electrode 23, the first negative electrode 24, and the second negative electrode 25 or one of the first positive electrode 22 and the second positive electrode 23 and one of the first negative electrode 24 and the second negative electrode 25 are separated from the body surface of the user, the resistance values R1 to R4 between each of the electrodes 22 to 25 separated from the body surface of the user and each of the electrodes 22 to 25 brought into contact with the body surface of the user become substantially infinite. Thus, the determining unit 62 can easily determine whether or not it is the state in which any one of the first positive electrode 22, the second positive electrode 23, the first negative electrode 24, and the second negative electrode 25 or one of the first positive electrode 22 and the second positive electrode 23 and one of the first negative electrode 24 and the second negative electrode 25 are separated from the body surface of the user, and the others of the first positive electrode 22, the second positive electrode 23, the first negative electrode 24, and the second negative electrode 25 or the other one of the first positive electrode 22 and the second positive electrode 23 and the other one of the first negative electrode 24 and the second negative electrode 25 are brought into contact with the body surface of the user. Thus, the antenna 45, the LED 46, and the buzzer 47 can send out information with a high degree of certainty when any one of the first positive electrode 22, the second positive electrode 23, the first negative electrode 24, and the second negative electrode 25 or one of the first positive electrode 22 and the second positive electrode 23 and one of the first negative electrode 24 and the second negative electrode 25 are separated from the body surface of the user, and the others of the first positive electrode 22, the second positive electrode 23, the first negative electrode 24, and the second negative electrode 25 or the other one of the first positive electrode 22 and the second positive electrode 23 and the other one of the first negative electrode 24 and the second negative electrode 25 are brought into contact with the body surface of the user.

The first positive electrode 22 is closer to the edge 31a of the attaching face 31 than the first negative electrode 24, and the second positive electrode 23 is farther from the edge 31a of the attaching face 31 than the second negative electrode 25. The electrodes 22 and 25 located at the outer side of the attaching face 31 are more likely to be peeled off than the electrodes 23 and 24 located at the inner side of the attaching face 31. For example, an external factor that weaken adhesion force between the double-sided tape 26 and the body surface of the user such as moisture tends to be infiltrated into the inside from the edge 31a of the attaching face 31. Thus, when the healthcare device 11 is peeled off from the body surface of the user, although the first positive electrode 22 and the second negative electrode 25 that are closer to the edge 31a of the attaching face 31 are separated from the body surface of the user, the second positive electrode 23 and the first negative electrode 24 are likely to be kept coming into contact with the body surface of the user. Thus, the heartbeat sensor 43 can continuously detect the biological information with the second positive electrode 23 and the first negative electrode 24.

The electric resistors 56 mutually change the resistance value R1 between the first positive electrode 22 and the first negative electrode 24, the resistance value R2 between the first positive electrode 22 and the second negative electrode 25, the resistance value R3 between the second positive electrode 23 and the first negative electrode 24, and the resistance value R4 between the second positive electrode 23 and the second negative electrode 25. Thus, it is possible to easily detect which one of the first positive electrode 22, the second positive electrode 23, the first negative electrode 24, and the second negative electrode 25 has been separated from the body surface of the user based on the resistance values R1 to R4 between the first and second positive electrodes 22 and 23 and the first and second negative electrodes 24 and 25.

The healthcare device 11 includes the LED 46 that emits light when at least one of the first positive electrode 22, the second positive electrode 23, the first negative electrode 24, and the second negative electrode 25 is separated from the body surface of the user, and the other or others of the first positive electrode 22, the second positive electrode 23, the first negative electrode 24, and the second negative electrode 25 are brought into contact with the body surface of the user. In other words, by emitting light through the LED 46, the healthcare device 11 sends out information indicating that it is in the state in which at least one of the first positive electrode 22, the second positive electrode 23, the first negative electrode 24, and the second negative electrode 25 is separated from the body surface of the user, and the other or others of the first positive electrode 22, the second positive electrode 23, the first negative electrode 24, and the second negative electrode 25 are brought into contact with the body surface of the user. As a result, the user can easily understand that the healthcare device 11 has been peeled off from the body surface of the user.

The healthcare device 11 includes the buzzer 47 that emits a sound when at least one of the first positive electrode 22, the second positive electrode 23, the first negative electrode 24, and the second negative electrode 25 is separated from the body surface of the user, and the other or others of the first positive electrode 22, the second positive electrode 23, the first negative electrode 24, and the second negative electrode 25 are brought into contact with the body surface of the user. In other words, by emitting a sound through the buzzer 47, the healthcare device 11 sends out information indicating that it is the state in which at least one of the first positive electrode 22, the second positive electrode 23, the first negative electrode 24, and the second negative electrode 25 is separated from the body surface of the user, and the other or others of the first positive electrode 22, the second positive electrode 23, the first negative electrode 24, and the second negative electrode 25 are brought into contact with the body surface of the user. As a result, the user can easily understand that the healthcare device 11 has been peeled off from the body surface of the user.

The antenna 45 of the healthcare device 11 outputs information to the first server 13 and the information terminal 12 when at least one of the first positive electrode 22, the second positive electrode 23, the first negative electrode 24, and the second negative electrode 25 is separated from the body surface of the user, and the other or others of the first positive electrode 22, the second positive electrode 23, the first negative electrode 24, and the second negative electrode 25 are brought into contact with the body surface of the user. For example, the information terminal 12 that has received the information displays information indicating that it is in the state in which at least one of the first positive electrode 22, the second positive electrode 23, the first negative electrode 24, and the second negative electrode 25 is separated from the body surface of the user, and the other or others of the first positive electrode 22, the second positive electrode 23, the first negative electrode 24, and the second negative electrode 25 are brought into contact with the body surface of the user, and thus the observer can easily understand that the healthcare device 11 has been peeled off from the body surface of the user.

The antenna 45, the LED 46, and the buzzer 47 send out information when the acceleration detected by the acceleration sensor 44 exceeds a threshold value. For example, when the user falls down, acceleration caused by the falling-down is detected by the acceleration sensor 44. Thus, for example, even when a plurality of electrodes, that is, the first positive electrode 22, the second positive electrode 23, the first negative electrode 24, and the second negative electrode 25 are separated from the body surface of the user at the same time, the user and/or the observer can understand that the healthcare device 11 has been peeled off from the body surface of the user due to a factor such as the falling-down based on the information sent out by the antenna 45, the LED 46, and the buzzer 47. Thus, the user and/or the observer can distinguish that the healthcare device 11 has been peeled off from the body surface of the user and that an abnormality has occurred in the user.

Each of the programs executed by the healthcare device 11 and the information terminal 12 according to the present embodiment is embedded in a ROM of the storage unit 42 or 72 in advance and provided.

Each of the programs executed by the healthcare device 11 and the information terminal 12 according to the present embodiment may be configured to be recorded a computer readable recording medium such as a CD-ROM, a flexible disk (FD), a CD-R, or a digital versatile disk (DVD) in an installable format or an executable format and provided.

Each of the programs executed by the healthcare device 11 and the information terminal 12 according to the present embodiment may be configured to be stored in a computer connected to a network such as the Internet and provided by downloading via a network. Each of the programs executed by the healthcare device 11 and the information terminal 12 according to the present embodiment may be configured to be provided or distributed via a network such as the Internet.

Each of the programs executed by the healthcare device 11 and the information terminal 12 according to the present embodiment has a module configuration including the above-described units (the obtaining control unit 61, the determining unit 62, the output control unit 63, the reception control unit 75, and the output control unit 76), and in actual hardware, as a CPU (processor) reads the corresponding program from the ROM and executes the read program, the respective units are loaded onto a main storage device, and each of the obtaining control unit 61, the determining unit 62, the output control unit 63, the reception control unit 75, and the output control unit 76 is generated on the main storage device.

Second Embodiment

A second embodiment will be described below with reference to FIGS. 11 to 13. In the following description of a plurality of embodiments, elements having the same function as the already described elements are denoted by the same reference numerals as the already described elements, and a description thereof may be omitted. Further, a plurality of elements having the same reference numeral do not necessarily have the same function and property, and may have different functions and properties according to each embodiment.

Figure 11:
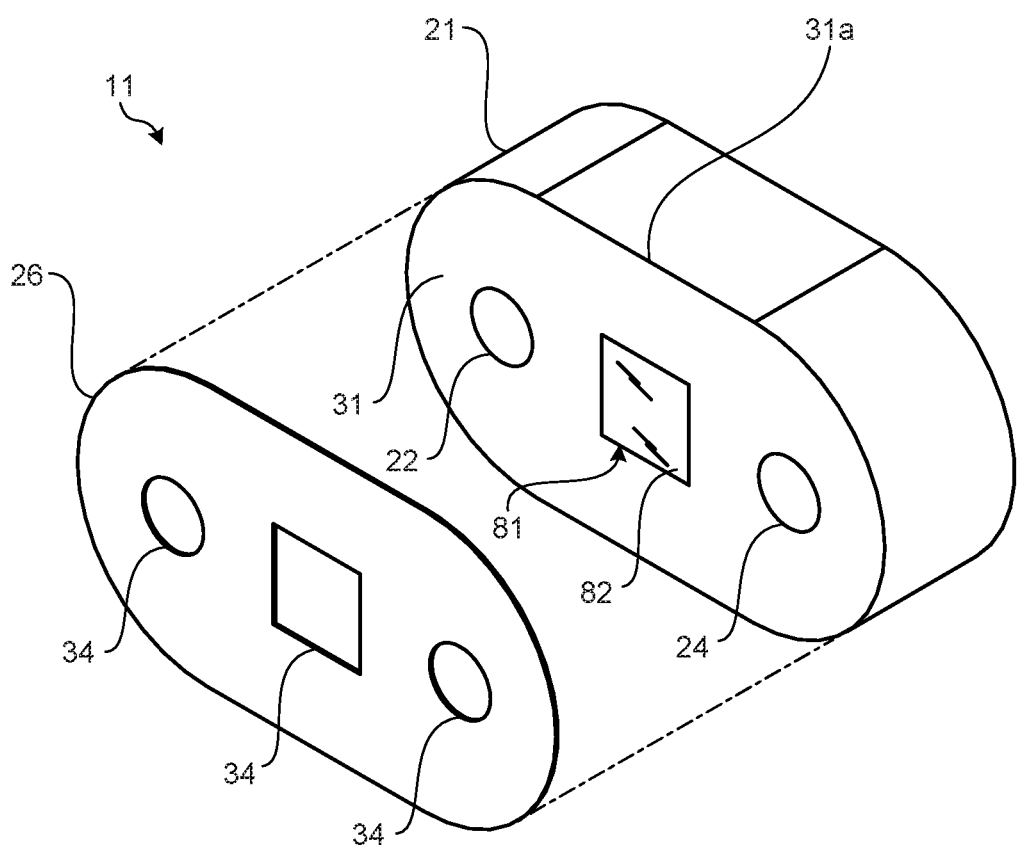
FIG. 11 is a perspective view illustrating a healthcare device according to a second embodiment.

FIG. 11 is a perspective view illustrating a healthcare device 11 according to a second embodiment. FIG. 12 is a block diagram illustrating an exemplary configuration of the healthcare device 11 according to the second embodiment. The healthcare device 11 according to the second embodiment includes an infrared sensor 81 instead of the second positive electrode 23 and the second negative electrode 25 as illustrated in FIG. 11. The infrared sensor 81 is an example of a sensing interface and a second sensing interface and can also be referred to as a sensor, a part, or a portion.

The infrared sensor 81 includes, for example, a photo-interrupter 82. The photo-interrupter 82 is provided on the attaching face 31 of the housing 21. The photo-interrupter 82 is positioned, for example, between the first positive electrode 22 and the first negative electrode 24. The photo-interrupter 82 may be provided at any other position.

In the present embodiment, the double-sided tape 26 is provided with three holes 34. Each of the holes 34 is larger than each of the first positive electrode 22, the first negative electrode 24, and the photo-interrupter 82. The three holes 34 expose the first positive electrode 22, the first negative electrode 24, and the photo-interrupter 82. Thus, when the attaching face 31 is attached to the chest of the user through the double-sided tape 26, the first positive electrode 22, the first negative electrode 24, and the photo-interrupter 82 come into contact with the chest of the user.

Figure 12:
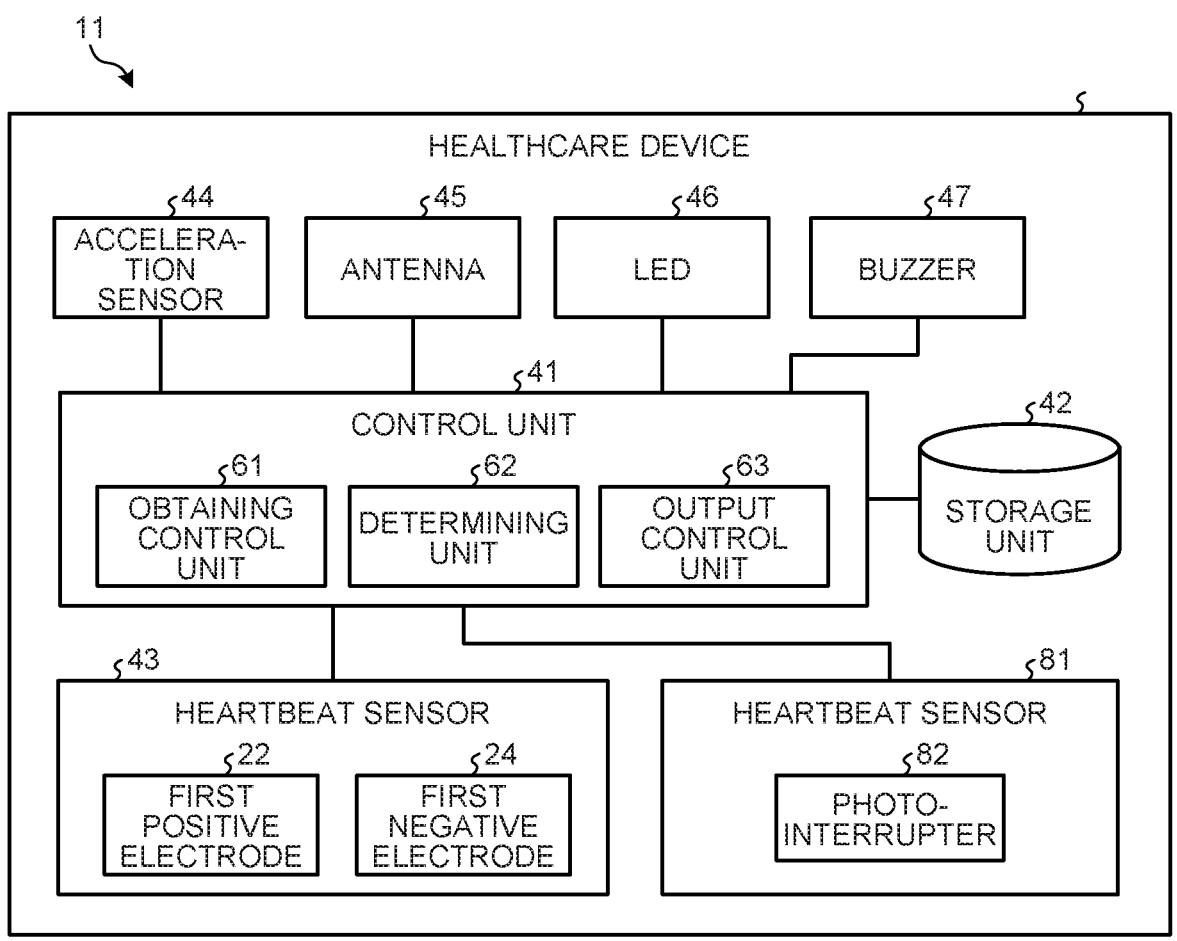
FIG. 12 is a block diagram illustrating an exemplary configuration of the healthcare device according to the second embodiment.

The heartbeat sensor 43 of the present embodiment illustrated in FIG. 12 obtains the heart action potential and the resistance value R1 from the first positive electrode 22 and the first negative electrode 24. The obtaining control unit 61 of the control unit 42 obtains the information related to the heart action potential and the resistance value R1 from the heartbeat sensor 43, generates the electrocardiogram, and calculates the heart rate of the user.

Meanwhile, the infrared sensor 81 irradiates the chest of the user coming into contact with the photo-interrupter 82 with infrared rays and receives reflected infrared rays, for example. The infrared sensor 81 detects a heartbeat of the user based on intensity of the received infrared rays. Unlike the heartbeat sensor 43 that obtains the heart action potential as described above, the infrared sensor 81 obtains the intensity of the infrared rays (the intensity of the reflected infrared rays) according to the blood flow of the user from the photo-interrupter 82. In other words, the infrared sensor 81 detects the intensity of the infrared rays with the photo-interrupter 82. The intensity of the reflected infrared rays is an example of second biological information. The obtaining control unit 61 of the control unit 41 obtains information according to the intensity of the reflected infrared rays from the infrared sensor 81, and calculates the heart rate of the user.

When at least one of the first positive electrode 22 and the first negative electrode 24 is separated from the chest of the user, the potential difference (the heart action potential) between the first positive electrode 22 and the first negative electrode 24 becomes 0 V. However, when the photo-interrupter 82 of the infrared sensor 81 comes into contact with the chest of the user, the infrared sensor 81 obtains the intensity of the reflected infrared rays. Thus, the obtaining control unit 61 can calculate the heart rate of the user based on the intensity of the reflected infrared rays.

On the other hand, when the photo-interrupter 82 of the infrared sensor 81 is separated from the chest of the user, the heart rate calculated from the intensity of the reflected infrared rays through the obtaining control unit 61 becomes substantially 0 (zero) times. However, when the first positive electrode 22 and the first negative electrode 24 come into contact with the chest of the user, the heartbeat sensor 43 obtains the heart action potential from the first positive electrode 22 and the first negative electrode 24. Thus, the obtaining control unit 61 can calculate the heart rate of the user based on the heart action potential.

As described above, when at least one of the first positive electrode 22 and the first negative electrode 24 of the heartbeat sensor 43 and the photo-interrupter 82 of the infrared sensor 81 is brought into contact with the chest of the user, the obtaining control unit 61 can continuously obtain the heart rate of the user.

Figure 13:
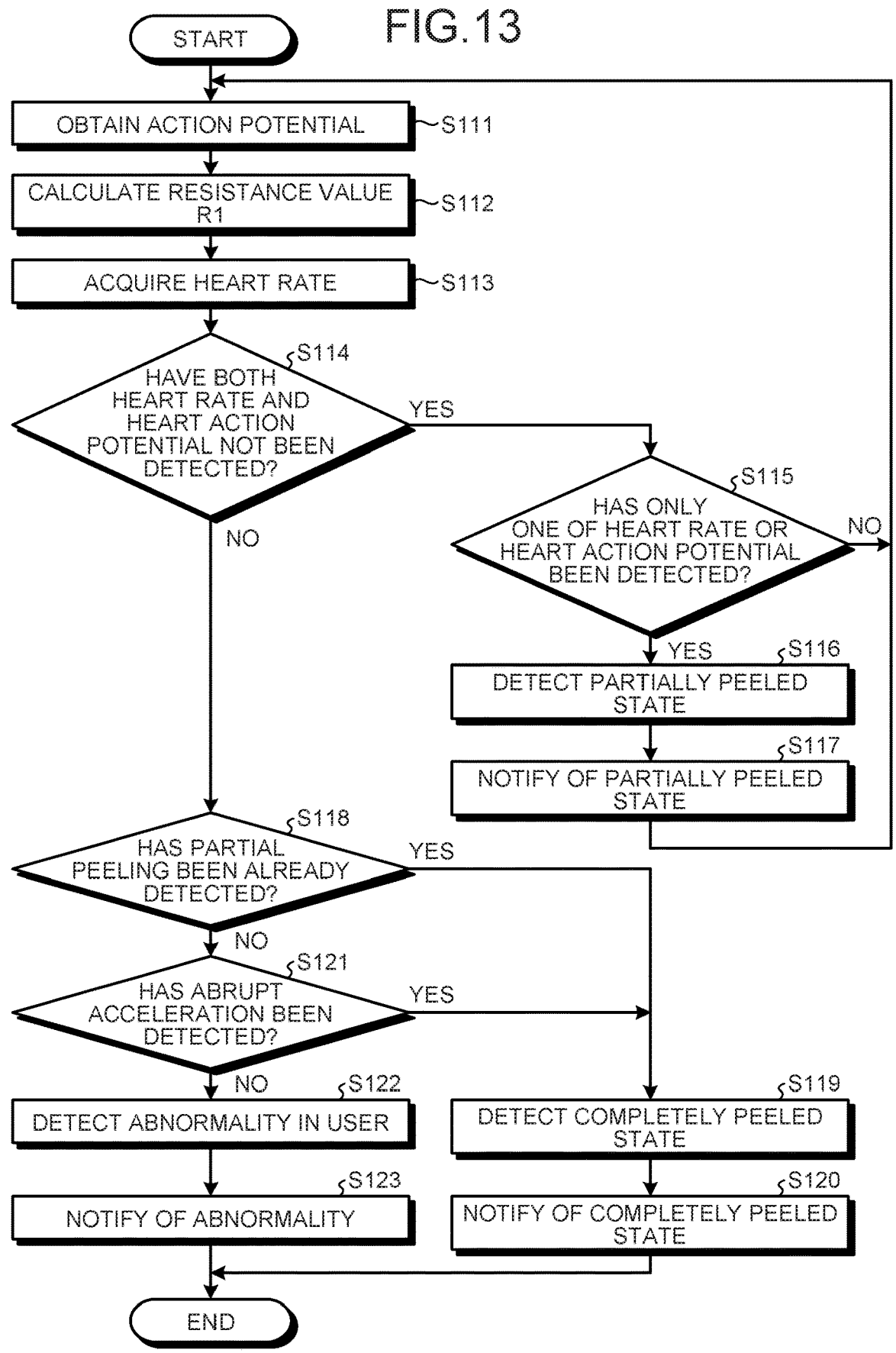
FIG. 13 is a flowchart illustrating a part of an abnormality detection process performed by the healthcare device according to the second embodiment.

FIG. 13 is a flowchart illustrating a part of an abnormality detection process performed by the healthcare device 11 according to the second embodiment. An example of the abnormality detection process executed by the healthcare device 11 will be described below with reference to the flowchart of FIG. 13.

First, the obtaining control unit 61 obtains the heart action potential of the user from the heartbeat sensor 43 (S111). Then, the obtaining control unit 61 calculates the resistance value R1 from the heart action potential (S112). Further, the obtaining control unit 61 obtains information according to the intensity of the reflected infrared rays from the infrared sensor 81, and calculates the heart rate of the user (S113).

Then, the determining unit 62 determines whether or not the obtaining control unit 61 has not detected both the heart rate of the user and the heart action potential (S114). For example, the determining unit 62 determines that the heart rate has not been detected when the heart rate obtained from the infrared sensor 81 is 0 (zero) times during a predetermined period of time. Further, the determining unit 62 determines that the heart action potential has not been detected when the heart action potential obtained from the heartbeat sensor 43 is substantially 0 V during a predetermined period of time. For example, the determining unit 62 determines that the heart action potential has not been detected when the heart action potential obtained from the heartbeat sensor 43 is lower than a previously set threshold value during a predetermined period of time. Further, when the resistance value R1 obtained from the heartbeat sensor 43 exceeds a threshold value, the determining unit 62 determines that the resistance value R1 becomes substantially infinite and thus determines that the heart action potential has not been detected.

When the determining unit 62 determines that at least one of the heart rate of the user and the heart action potential has been detected (S114: Yes), the determining unit 62 determines whether or not the obtaining control unit 61 has not detected the heart rate of the user or the heart action potential (S115). In other words, the determining unit 62 determines whether or not one of the heart rate of the user and the heart action potential has been detected, but the other of the heart rate and the heart action potential has not been detected.

When the determining unit 62 determines that one of the heart rate of the user and the heart action potential has been detected, but the other of the heart rate and the heart action potential has not been detected (S115: Yes), the determining unit 62 detects the partially peeled state (S116). The output control unit 63 notifies, for example, the user and the observer of the partially peeled state (S117).

When the user and the observer are notified of that it is the partially peeled state, the obtaining control unit 61 obtains the heart action potential again (S111). Similarly, when the determining unit 62 determines that both of the heart rate of the user and the heart action potential have been detected in S115 (S115: No), the obtaining control unit 61 obtains the heart action potential again (S111).

When the determining unit 62 determines that both of the heart rate of the user and the heart action potential have not been detected in S114 (S114: No), the determining unit 62 determines whether or not the partial peeling has been already detected (S118). When the partially peeled state has been already detected (S118: Yes), the determining unit 62 detects the completely peeled state (S119). When the completely peeled state is detected, the output control unit 63 notifies, for example, the user and the observer of that it is the completely peeled state (S120).

On the other hand, when the partially peeled state is not detected in S118 (S118: No), the determining unit 62 determines whether or not the acceleration sensor 44 has detected the abrupt acceleration (S121). When the acceleration sensor 44 has detected the abrupt acceleration (S121: Yes), the determining unit 62 detects the completely peeled state (S119). S121 may be omitted.

When the acceleration sensor 44 has not detected the abrupt acceleration (S121: No), the determining unit 62 detects an abnormality in the user (S122). The output control unit 63 notifies, for example, the person around the user and the observer of the abnormality in the user (S123).

As described above, the healthcare device 11 detects the abnormality in the user and the abnormality in the attaching state of the healthcare device 11 based on the heart action potentials obtained from the first positive electrode 22 and the first negative electrode 24 and the intensity of the reflected infrared rays obtained from the photo-interrupter 82 of the infrared sensor 81. In other words, the heartbeat sensor 43 of the healthcare device 11 obtains the heart action potential and the intensity of the reflected infrared rays as the information related to the contact state between the first positive electrode 22, the first negative electrode 24, and the photo-interrupter 82 and the chest of the user.

Similarly to the first embodiment, when it is the partially peeled state or the completely peeled state or when the abnormality occurs in the user, the antenna 45 outputs information to the first server 13. Further, by emitting light through the LED 46, the LED 46 sends out information for notifying of the contact state of the healthcare device 11 or the health state of the user. Furthermore, by emitting a sound through the buzzer 47, the buzzer 47 sends out information for notifying of the contact state of the healthcare device 11 or the health state of the user.

The abnormality detection process described above is performed by only the healthcare device 11. However, similarly to the first embodiment, the abnormality detection process may be performed by at least one of the healthcare device 11, the information terminal 12, the first server 13, and the second server 14.

In the healthcare device 11 according to the second embodiment, each of the antenna 45, the LED 46, and the buzzer 47 send out information when one of the first positive electrode 22 and the first negative electrode 24 of the heartbeat sensor 43 and the photo-interrupter 82 of the infrared sensor 81 is separated from the body surface of the user, and the other of the first positive electrode 22 and the first negative electrode 24 of the heartbeat sensor 43 and the photo-interrupter 82 of the infrared sensor 81 is brought into contact with the body surface of the user. Thus, when the first positive electrode 22, the first negative electrode 24, and the photo-interrupter 82 are brought into contact with the body surface of the user, the obtaining control unit 61 can obtain the heart action potential and the intensity of the reflected infrared rays that are two types of biological information. Further, the user and/or the observer can understand that the healthcare device 11 has been peeled off from the body surface of the user based on the information sent out by the antenna 45, the LED 46, and the buzzer 47.

The heartbeat sensor 43 detects the action potential of the user with the first positive electrode 22 and the first negative electrode 24. It is further beneficial if the user can distinguish that the healthcare device 11 has been peeled off from the body surface of the user and that an abnormality has occurred in the body surface of the user when the heartbeat sensor 43 detects the heart action potential as described above. For example, a possibility that the user will misunderstand the situation in which the healthcare device 11 has been peeled off from the body surface of the user as the abnormality in the user such as a cardiopulmonary arrest is reduced.

Third Embodiment

Figure 14:
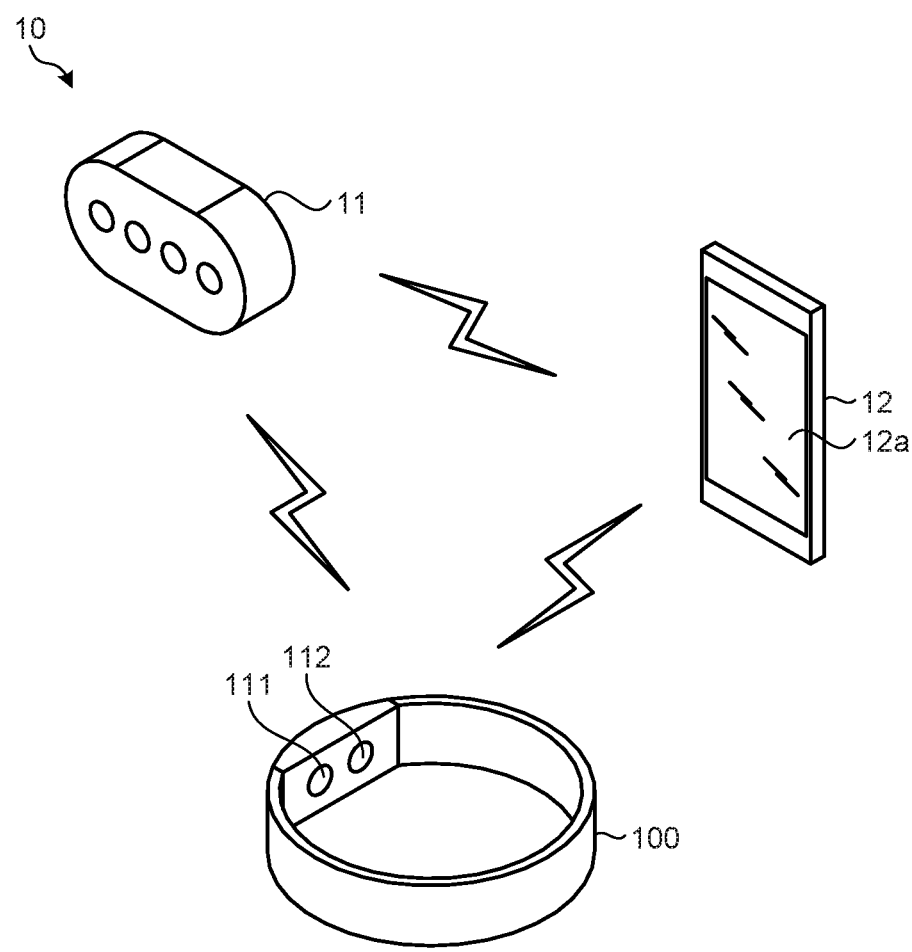
FIG. 14 is a diagram schematically illustrating a configuration of a monitoring system according to a third embodiment.

A third embodiment will be described below with reference to FIGS. 14 to 17. FIG. 14 is a diagram schematically illustrating a configuration of a monitoring system 10 according to the third embodiment. The monitoring system 10 according to the third embodiment is configured such that the healthcare device 11, the information terminal 12, a plurality of first servers 13, a plurality of second servers 14, and a wearable device 100 illustrated in FIG. 14 are connected. In FIG. 14, the first and second servers 13 and 14 are not illustrated.

The wearable device 100 is an example of another electronic device and can also be referred to as, for example, a monitoring device, a sensor, an apparatus, or a device. The wearable device 100 is, for example, a device of a wristwatch type and wore, for example, on the arm of the user. The wearable device 100 is not limited to this example and may be any other wearable device such as a band type or a spectacle type.

The wearable device 100 detects the heart rate of the user, similarly to the healthcare device 11. The wearable device 100 may obtain biological information of the user different from that of the healthcare device 11. For example, the wearable device 100 may obtain a blood pressure, a body temperature, or a sweat rate of the user. In other words, the wearable device 100 may detect a blood pressure, a body temperature, or a sweat rate of the user. The wearable device 100 of the present embodiment transmits information related to the detected heart rate to the information terminal 12 and the first server 13 directly or via a relay device.

Figure 15:
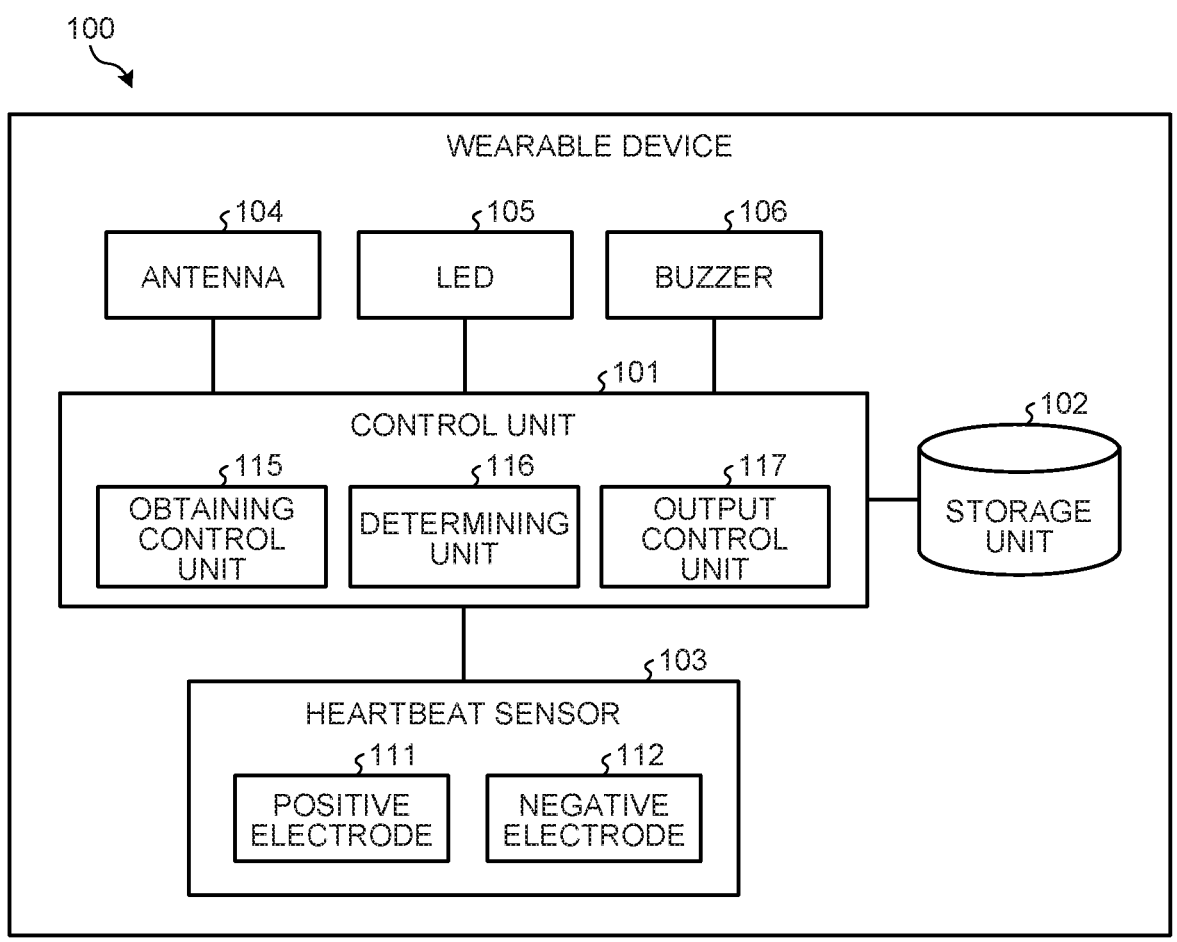
FIG. 15 is a block diagram illustrating an exemplary configuration of a wearable device according to the third embodiment.

FIG. 15 is a block diagram illustrating an exemplary configuration of the wearable device 100 according to the third embodiment. The wearable device 100 includes a control unit 101, a storage unit 102, a heartbeat sensor 103, an antenna 104, an LED 105, and a buzzer 106 as illustrated in FIG. 15. The control unit 101 can also be referred to as, for example, a control device or a control circuit.

The control unit 101 controls various kinds of operations in the wearable device 100 in general. The control unit 101 is, for example, a microprocessor equipped with a CPU therein. The control unit 101 is not limited to this example and may be any other device. For example, each of the functions of the control unit 101 may be implemented by each of portions or a collaboration of a plurality of portions distributed in a circuit including various electronic parts. The storage unit 102 stores information that is used by the control unit 101. For example, the storage unit 102 includes a ROM that stores a control program executed by the CPU with which the control unit 101 is equipped therein, a RAM that provides a work area to the CPU, and a non-volatile memory that stores various kinds of information.

The heartbeat sensor 103 includes a positive electrode 111 and a negative electrode 112. For example, the heartbeat sensor 103 obtains the heart action potential of the user from the positive electrode 111 and the negative electrode 112 in the arm of the user. In other words, the heartbeat sensor 103 detects the heart action potential of the user with the positive electrode 111 and the negative electrode 112 in the arm of the user. The heartbeat sensor 103 of the wearable device 100 obtains the heart action potential at the position (arm) separated from the first and second positive electrodes 22 and 23 and the first and second negative electrodes 24 and 25 of the healthcare device 11.

For example, the positive electrode 111 and the negative electrode 112 come into contact with the arm of the user and thus are electrically connected to each other through the arm (the body surface) of the user. The heartbeat sensor 103 obtains the heart action potential in the arm, for example, through the two-terminal sensing.

The antenna 104 is an antenna for performing wireless communication, for example, via wireless network such as a wireless LAN, the Bluetooth, or a 3G network. The LED 105 is controlled by the control unit 101 and emits light. The buzzer 106 is controlled by the control unit 101 and emits a sound.

The control unit 101 implements an obtaining control unit 115, a determining unit 116, and an output control unit 117, for example, through a collaboration with a program stored in the storage unit 102. The control unit 101 may implement any other functional configuration.

The obtaining control unit 115 obtains the heart action potential described above from the heartbeat sensor 103. In other words, the obtaining control unit 115 receives the heart action potential from the heartbeat sensor 103. The obtaining control unit 115 generates the electrocardiogram based on the obtained heart action potential. The obtaining control unit 115 calculates the heart rate of the user from the generated electrocardiogram. The obtaining control unit 115 outputs, for example, the information related to the electrocardiogram and the heart rate to the output control unit 117.

The determining unit 116 determines whether or not the positive electrode 111 and the negative electrode 112 have been separated from the arm of the user. For example, when the potential difference (the heart action potential) between the positive electrode 111 and the negative electrode 112 becomes substantially 0 V, the determining unit 116 determines that the positive electrode 111 and the negative electrode 112 have been separated from the arm of the user. The determining unit 116 may determine that the positive electrode 111 and the negative electrode 112 have been separated from the arm of the user when the resistance value between the positive electrode 111 and the negative electrode 112 becomes substantially infinite.

The output control unit 117 controls, for example, the antenna 104 such that the information related to the electrocardiogram and the heart rate obtained from the obtaining control unit 115 is transmitted to the first server 13. The first server 13 transmits the received information related to the electrocardiogram and the heart rate to the information terminal 12 of the observer. The information terminal 12 causes the received information related to the electrocardiogram and the heart rate to be displayed on the display unit 12a. As a result, the observer can understand the information related to the electrocardiogram and the heart rate of the user.

Further, the output control unit 117 obtains the determination result from the determining unit 116. In other words, the output control unit 117 receives the determination result from the determining unit 116. For example, when the determining unit 116 determines that the positive electrode 111 and the negative electrode 112 have separated from the arm of the user, the output control unit 117 controls the antenna 104 such that the determination result is transmitted to the first server 13. In other words, when the positive electrode 111 and the negative electrode 112 have been separated from the arm of the user, the antenna 45 outputs information to the first server 13.

Figure 16:
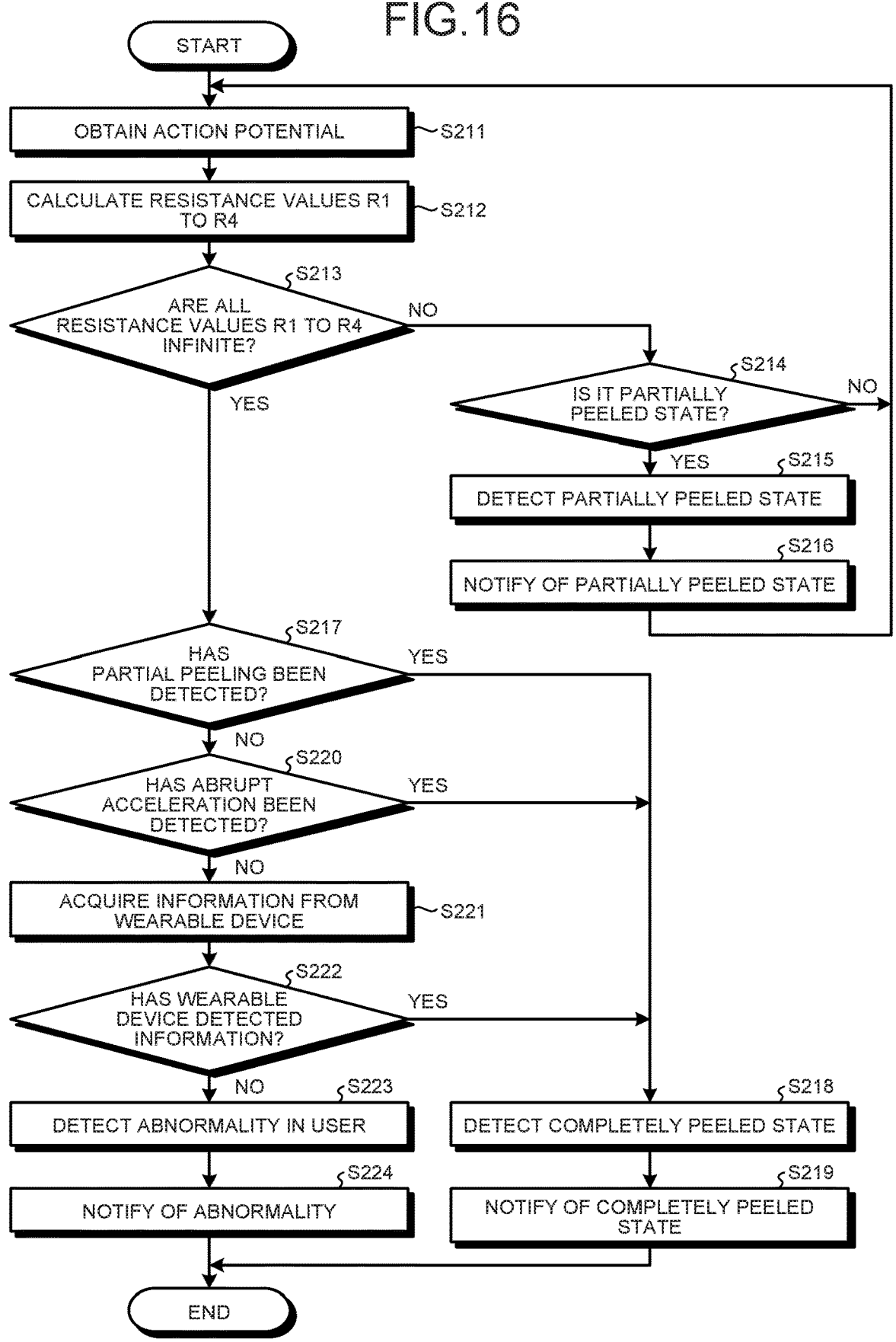
FIG. 16 is a flowchart illustrating a part of an abnormality detection process performed by a healthcare device according to the third embodiment.

FIG. 16 is a flowchart illustrating a part of an abnormality detection process performed by the healthcare device 11 according to the third embodiment. An example of the abnormality detection process executed by the healthcare device 11 will be described below with reference to the flowchart of FIG. 16.

First, the obtaining control unit 61 obtains the heart action potentials of the user from the heartbeat sensor 43 (S211). Then, the obtaining control unit 61 calculates the resistance values R1 to R4 from the heart action potentials (S212).

Then, the determining unit 62 determines whether or not all the resistance values R1 to R4 are substantially infinite (S213). When any one of the resistance values R1 to R4 is not substantially infinite (S213: No), the determining unit 62 determines whether or not it is the partially peeled state (S214).

When any one of the resistance values R1 to R4 or one of the resistance value R1 and the resistance value R2 and one of the resistance value R3 and the resistance value R4 are substantially infinite (S214: Yes), the determining unit 62 detects the partially peeled state (S215). The output control unit 63 notifies, for example, the user and the observer of that it is the partially peeled state (S216).

When the user and the observer are notified of the partially peeled state, the obtaining control unit 61 obtains the heart action potential again (S211). Similarly, when all of the resistance values R1 to R4 is not substantially infinite in S214 (S214: No), the obtaining control unit 61 obtains the heart action potential again (S211).

When the determining unit 62 determines that all the resistance values R1 to R4 are substantially infinite in S213 (S213: Yes), the determining unit 62 determines whether or not the partial peeling has been already detected (S217). When the partially peeled state has been already detected (S217: Yes), the determining unit 62 detects the completely peeled state (S218).

When the completely peeled state is detected, the output control unit 63 notifies, for example, the user and the observer of that it is the completely peeled state (S219).

On the other hand, when the partially peeled state is not detected in S217 (S217: No), the determining unit 62 determines whether or not the acceleration sensor 44 has detected the abrupt acceleration (S220). When the acceleration sensor 44 has detected the abrupt acceleration (S220: Yes), the determining unit 62 detects the completely peeled state (S218). S220 may be omitted.

When the acceleration sensor 44 has not detected the abrupt acceleration (S220: No), the obtaining control unit 61 controls the antenna 45 such that the information related to the electrocardiogram and the heart rate is obtained from the wearable device 100 (S221). For example, the antenna 45 of the healthcare device 11 receives a signal of the information related to the electrocardiogram and the heart rate that is transmitted from the wearable device 100 to the first server 13. The information related to the electrocardiogram and the heart rate is an example of the biological information. The antenna 45 of the healthcare device 11 may receive the signal of the information related to the electrocardiogram and the heart rate directly from the antenna 104 of the wearable device 100.

Then, the determining unit 62 determines whether or not the wearable device 100 has detected the electrocardiogram and the heart rate (S222). For example, when the heart rate received from the wearable device 100 is larger than one time, the determining unit 62 determines that the wearable device 100 has detected the electrocardiogram and the heart rate (S222: Yes).

When the healthcare device 11 is in the completely separated state, all the resistance values R1 to R4 are substantially infinite, and the potential difference (the heart action potential) detected from the first positive electrode 22, the second positive electrode 23, the first negative electrode 24, and the second negative electrode 25 is 0 V.

However, when the positive electrode 111 and the negative electrode 112 of the wearable device 100 come into contact with the arm of the user, and the state of the user is normal, the wearable device 100 continuously detects the electrocardiogram and the heart rate.

As described above, when the wearable device 100 has detected the electrocardiogram and the heart rate, although the potential difference detected from the first positive electrode 22, the second positive electrode 23, the first negative electrode 24, and the second negative electrode 25 of the healthcare device 11 is 0 V, the user can be estimated to be in the normal state. Thus, when the wearable device 100 has detected the electrocardiogram and the heart rate (S222: Yes), the determining unit 62 detects the completely peeled state (S218).

When the wearable device 100 detects the electrocardiogram and the heart rate, and the determining unit 62 detects the completely peeled state, the output control unit 63 notifies, for example, the user and the observer of that it is the completely peeled state (S219). As described above, when the first positive electrode 22, the second positive electrode 23, the first negative electrode 24, and the second negative electrode 25 of the healthcare device 11 are separated from the chest of the user, and the positive electrode 111 and the negative electrode 112 of the wearable device 100 come into contact with the arm of the user, each of the antenna 45, the LED 46, and the buzzer 47 send out information.

On the other hand, for example, when the heart rate received from the wearable device 100 is 0 (zero) times during a predetermined period of time, the determining unit 62 determines that the wearable device 100 has not detected the electrocardiogram and the heart rate (S222: No). In this case, the determining unit 62 detects the abnormality in the user (S223). The output control unit 63 notifies, for example, the person around the user and the observer of the abnormality in the user (S224).

As described above, the healthcare device 11 detects an abnormality in the user and an abnormality in the attaching state of the healthcare device 11 based on the resistance values R1 to R4 and the information related to the electrocardiogram and the heart rate obtained from the wearable device 100.

The abnormality detection process described above is performed by only the healthcare device 11. However, similarly to the first embodiment, the abnormality detection process may be performed by at least one of the healthcare device 11, the information terminal 12, the first server 13, and the second server 14.

The healthcare device 11 of the third embodiment described above can detect an abnormality in a attaching position of the healthcare device 11 as well as the abnormality in the user and the abnormality in the attaching state the healthcare device 11 and the wearable device 100.

For example, the obtaining control unit 61 of the healthcare device 11 generates the electrocardiogram from the heart action potential obtained from the heartbeat sensor 43. Further, the obtaining control unit 61 obtains information related to the electrocardiogram from the wearable device 100. In other words, the obtaining control unit 61 receives information related to the electrocardiogram from the wearable device 100.

The waveform of the electrocardiogram generated by the healthcare device 11 is almost identical to the waveform of the electrocardiogram obtained from the wearable device 100. However, a distance between the heart of the user and the position (chest) at which the healthcare device 11 is attached is different from a distance between the heart of the user and the position (arm) at which the wearable device 100 is attached. Thus, there is a time difference between the waveform of the electrocardiogram generated by the healthcare device 11 and the waveform of the electrocardiogram obtained from the wearable device 100.

For example, when the healthcare device 11 and the wearable device 100 of the third embodiment are initially used by the user, the time difference between the electrocardiogram generated by the healthcare device 11 and the electrocardiogram obtained from the wearable device 100 is stored in the storage unit 42 of the healthcare device 11. The determining unit 62 of the healthcare device 11 can determine whether or not the healthcare device 11 is attached at substantially the same position as that of the first time by comparing the time difference stored in the storage unit 42 with the time difference between the electrocardiogram of the healthcare device 11 and the electrocardiogram of the wearable device 100.

FIG. 17 is a flowchart illustrating a part of a attaching position detection process performed by the healthcare device 11 according to the third embodiment. An example of the attaching position detection process executed by the healthcare device 11 will be described below with reference to the flowchart of FIG. 17.

First, the obtaining control unit 61 obtains the heart action potentials of the user from the heartbeat sensor 43 (S311). Then, the obtaining control unit 61 generates the electrocardiograms from the respective heart action potentials (S312). The obtaining control unit 61 controls the antenna 45 such that the information related to the electrocardiogram is obtained from the wearable device 100 (S313).

Then, the obtaining control unit 61 calculates the time difference between the generated electrocardiogram and the electrocardiogram obtained from the wearable device 100 (S314). For example, the obtaining control unit 61 calculates a time difference between a P wave of the generated electrocardiogram and a P wave of the electrocardiogram obtained from the wearable device 100. The obtaining control unit 61 outputs the calculated time difference to the determining unit 62.

Then, the obtaining control unit 61 reads a time difference stored in the storage unit 42 from the storage unit 42 (S315). The time difference stored in the storage unit 42 may be stored, for example, when the healthcare device 11 and the wearable device 100 are initially used by the user or may be stored when the healthcare device 11 and the wearable device 100 are previously used. The obtaining control unit 61 outputs the read time difference to the determining unit 62.

Then, the determining unit 62 determines whether or not the calculated time difference is within a determination range (S316). For example, the determination range is a range in which a value obtained by subtracting a predetermined value from the time difference read from the storage unit 42 is set as a lower limit, and a value obtained by adding a predetermined value to the time difference read from the storage unit 42 is set as an upper limit. The determination range is not limited to this example.

When the calculated time difference is within the determination range (S316: Yes), the output control unit 63 notifies of that the healthcare device 11 is mounted at a correct position (S317). For example, the output control unit 63 controls the LED 46 such that the LED 46 is turned on during a predetermined period of time. In other words, by emitting light through the LED 46, LED 46 sends out information for notifying of the contact state of the healthcare device 11. The output control unit 63 may control the antenna 45 and the buzzer 47 such that information for notifying the antenna 45 and the buzzer 47 of the contact state of the healthcare device 11 is sent out.

When the calculated time difference is out of the determination range (S316: No), the output control unit 63 notifies of a deviation in the position of the healthcare device 11 (S318). For example, the output control unit 63 controls the LED 46 such that the LED 46 blinks. In other words, by emitting light through the LED 46, the LED 46 sends out information for notifying of the contact state of the healthcare device 11. The output control unit 63 may control the antenna 45 and the buzzer 47 such that information for notifying the antenna 45 and the buzzer 47 of the contact state of the healthcare device 11 is sent out.

As described above, when the time difference between the electrocardiogram obtained from the first and second positive electrodes 22 and 23 and the first and second negative electrodes 24 and 25 and the electrocardiogram obtained by the wearable device 100 is out of the determination range, the healthcare device 11 detects the abnormality in the attaching state (the position deviation) of the healthcare device 11. In other words, the heartbeat sensor 43 of the healthcare device 11 obtains the heart action potential as the information related to the contact state between the first positive electrode 22, the second positive electrode 23, the first negative electrode 24, and the second negative electrode 25 and the chest of the user.

The attaching position detection process is performed by only the healthcare device 11. However, the attaching position detection process may be performed by at least one of the healthcare device 11, the information terminal 12, the first server 13, the second server 14, and the wearable device 100.

In the healthcare device 11 and the wearable device 100 of the third embodiment, the antenna 45, the LED 46, and the buzzer 47 send out information when one of the first positive electrode 22, the second positive electrode 23, the first negative electrode 24, and the second negative electrode 25 and the wearable device 100 is separated from the body surface of the user, and the other of the first positive electrode 22, the second positive electrode 23, the first negative electrode 24, and the second negative electrode 25 and the wearable device 100 are brought into contact with the body surface of the user. When one of the first positive electrode 22, the second positive electrode 23, the first negative electrode 24, and the second negative electrode 25 and the wearable device 100 is separated from the body surface of the user, the biological information detected with the first positive electrode 22, the second positive electrode 23, the first negative electrode 24, and the second negative electrode 25 or the wearable device 100 separated from the body surface of the user is abnormal, but the biological information detected with the first positive electrode 22, the second positive electrode 23, the first negative electrode 24, and the second negative electrode 25 or the wearable device 100 coming into contact with the body surface of the user is normal. As a result, it can be understood that the healthcare device 11 or the wearable device 100 has been peeled off from the body surface of the user in real time or later based on the biological information detected with the first positive electrode 22, the second positive electrode 23, the first negative electrode 24, and the second negative electrode 25 and the wearable device 100. Thus, it is possible to distinguish that the healthcare device 11 or the wearable device 100 has been peeled off from the body surface of the user and that an abnormality has occurred in the user.

The time difference between the biological information of the user detected with the first positive electrode 22, the second positive electrode 23, the first negative electrode 24, and the second negative electrode 25 by the heartbeat sensor 43 and the biological information of the user detected by the wearable device 100 differs according to the positions of the first positive electrode 22, the second positive electrode 23, the first negative electrode 24, and the second negative electrode 25 with respect to the wearable device 100. Each of the antenna 45, the LED 46, and the buzzer 47 sends out information when the time difference between the biological information of the user detected with the first positive electrode 22, the second positive electrode 23, the first negative electrode 24, and the second negative electrode 25 by the heartbeat sensor 43 and the biological information of the user detected by the wearable device 100 is out of the determination range. Thus, each of the antenna 45, the LED 46, and the buzzer 47 can urge the user to the first positive electrode 22, the second positive electrode 23, the first negative electrode 24, and the second negative electrode 25 of the healthcare device 11 to be brought into contact with the correct position (for example, the positions at which the first positive electrode 22, the second positive electrode 23, the first negative electrode 24, and the second negative electrode 25 are brought into contact with the body surface of the user when the time difference is stored in the storage unit 42). As a result, the reliability of the biological information detected by the heartbeat sensor 43 is further improved.

In the plurality of above-described embodiments, each of the antenna 45, the LED 46, and the buzzer 47 is an example of each of the first to fourth output units, and sends out information substantially in real time when at least one of the first positive electrode 22, the second positive electrode 23, the first negative electrode 24, and the second negative electrode 25 is separated from the body surface of the user. However, for example, the output control unit 63 of the control unit 41 may output the information related to the determination result to be stored in the storage unit 42 as an example of each of the first to fourth output units when at least one of the first positive electrode 22, the second positive electrode 23, the first negative electrode 24, and the second negative electrode 25 is separated from the body surface of the user. For example, the user and the observer can understand that at least one of the first positive electrode 22, the second positive electrode 23, the first negative electrode 24, and the second negative electrode 25 has been separated from the body surface of the user later by checking the information related to the determination result stored in the storage unit 42. As described above, each of the first to fourth output units may be a component or a circuit, for example. However, each of the first to fourth output units may be a program. A circuit such as the control unit 41 may read the program from a ROM and execute the read program.

In the plurality of above-described embodiments, the healthcare device 11 is an example of the electronic device. However, the electronic device may be a device that is attached to another machine, for example. In this case, each of the antenna 45, the LED 46, and the buzzer 47 sends out information when at least one of the first positive electrode 22, the second positive electrode 23, the first negative electrode 24, and the second negative electrode 25 is separated from the surface of the machine.

Further, in the plurality of above-described embodiments, the housing 21 is an example of an attaching member. However, the attaching member may be another member such as a film or a substrate. In this case, for example, the first positive electrode 22, the second positive electrode 23, the first negative electrode 24, the second negative electrode 25, the control unit 41, the storage unit 42, the heartbeat sensor 43, the acceleration sensor 44, the antenna 45, the LED 46, and the buzzer 47 are provided on the attaching member.

According to at least one of the above-described embodiments, the term, "obtain" is considered to include the meanings of "detect", "sense", "receive", or "calculate", for example. For example, in the first embodiment, the heartbeat sensor 43 is configured to obtain the action potential, sense or detect the potential difference as the heart action potential with the first positive electrode 22, the second positive electrode 23, the first negative electrode 24, and the second negative electrode 25, and output an electric signal according to the heart action potential. The heartbeat sensor 43 may calculate the heat action potential based on other physical properties and/or information, for example.

According to at least one of the above-described embodiments, the term, "output" is considered to represent "emit light, sound or the like" or "send information", for example. Furthermore, it is also considered to represent "display a text and/or an image".

According to at least one of the above-described embodiments, an electronic device including a sensing circuit and an output unit is provided. The sensing circuit is configured to obtain information related to the contact state between a plurality of sensing interfaces of another device and the detection target. The output unit is configured to output information indicating that at least one of the plurality of sensing interfaces has been separated from the detection target based on the obtained information related to the contact state.

According to at least one of the above-described embodiments, the sensing circuit obtains the information related to the contact state between the sensing interface and the detection target from the sensing interface. As a result, the abnormality in the contact state between the sensing interface and the detection target can be understood based on the information related to the contact state.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An electronic device, comprising:
    an attaching member comprising a face configured to be attached to a detection target;
    a sensing circuit comprising a plurality of sensing interfaces provided on the face, the sensing circuit configured to detect at least one type of biological information of the detection target with the sensing interfaces; and
    a first output unit configured to send out information when at least one of the sensing interfaces is separated from the detection target and the other or others of the sensing interfaces are brought into contact with the detection target, wherein the plurality of sensing interfaces comprises a plurality of electrodes, the electrodes comprise a first positive electrode, a second positive electrode, a first negative electrode, and a second negative electrode, the first negative electrode configured to be connected in parallel to the first positive electrode and the second positive electrode through the detection target, the second negative electrode configured to be connected in parallel to the first positive electrode and the second positive electrode through the detection target, the first positive electrode, the second positive electrode, the first negative electrode, and the second negative electrode are arranged side by side in a direction, the first positive electrode is closer to an edge of the face than the first negative electrode, the second positive electrode is farther from the edge of the face than the second negative electrode, the second positive electrode and the first negative electrode are arranged between the first positive electrode and the second negative electrode, and the first output unit is configured to send out the information when:

any one of the first positive electrode, the second positive electrode, the first negative electrode, and the second negative electrode is separated from the detection target, and the rest of the first positive electrode, the second positive electrode, the first negative electrode, and the second negative electrode are in contact with the detection target, or one of the first positive electrode and the second positive electrode and one of the first negative electrode and the second negative electrode are separated from the detection target, and the other of the first positive electrode and the second positive electrode and the other of the first negative electrode and the second negative electrode are in contact with the detection target.

2. The electronic device according to claim 1, wherein the sensing circuit is configured to detect an action potential of the detection target with the first positive electrode, the second positive electrode, the first negative electrode, and the second negative electrode.

3. The electronic device according to claim 1, further comprising:
an acceleration sensor configured to detect acceleration; and
a second output unit configured to send out information when the acceleration exceeds a threshold value.

4. The electronic device according to claim 1, wherein the first output unit comprises a light emitting component configured to emit light when at least one of the sensing interfaces is separated from the detection target and the other or others of the sensing interfaces are brought into contact with the detection target.

5. The electronic device according to claim 3, wherein the first output unit comprises a sounding component configured to emit a sound when at least one of the sensing interfaces is separated from the detection target, and the other or others of the sensing interfaces are brought into contact with the detection target.

6. The electronic device according to claim 3, wherein the first output unit is configured to output information to another device when at least one of the sensing interfaces is separated from the detection target and the other or others of the sensing interfaces are brought into contact with the detection target.

7. The electronic device according to claim 1, further comprising:
a receiving component configured to receive the biological information from another electronic device configured to detect at least one type of the biological information of the detection target at a position separated from the sensing interfaces, wherein
the first output unit is configured to send out the information when one of the sensing interfaces and the other electronic device is separated from the detection target and the other of the sensing interfaces and the other electronic device are brought into contact with the detection target.

8. The electronic device according to claim 7, further comprising:
a third output unit configured to send out information when a time difference between the biological information of the detection target detected by the sensing circuit with at least one of the sensing interfaces and the biological information of the detection target detected by the other electronic device is out of a determination range.

9. The electronic device according to claim 1, further comprising:
a receiving component configured to receive the biological information from another electronic device configured to detect at least one type of the biological information of the detection target at a position separated from the sensing interfaces; and
a fourth output unit configured to send out information when a time difference between the biological information of the detection target detected by the sensing circuit with at least one of the sensing interfaces and the biological information of the detection target detected by the other electronic device is out of a determination range.

10. An electronic device, comprising:
an attaching member comprising a face configured to be attached to a detection target; and
a sensing circuit comprising a plurality of sensing interfaces provided on the face, the sensing circuit configured to detect at least one type of biological information of the detection target with the sensing interfaces, wherein
the plurality of sensing interfaces comprises a plurality of electrodes,
the electrodes comprise a first positive electrode, a second positive electrode, a first negative electrode, and a second negative electrode, the first negative electrode configured to be connected in parallel to the first positive electrode and the second positive electrode through the detection target, the second negative electrode configured to be connected in parallel to the first positive electrode and the second positive electrode through the detection target,
the first positive electrode, the second positive electrode, the first negative electrode, and the second negative electrode are arranged side by side in a direction,
the first positive electrode is closer to an edge of the face than the first negative electrode,
the second positive electrode is farther from the edge of the face than the second negative electrode, and
the second positive electrode and the first negative electrode are arranged between the first positive electrode and the second negative electrode.

11. An electronic device, comprising:
an attaching member comprising a face configured to be attached to a detection target; and
a sensing circuit comprising a plurality of sensing interfaces provided on the face, the sensing circuit configured to obtain information related to a contact state between the sensing interfaces and the detection target from the sensing interfaces, wherein
the plurality of sensing interfaces comprises a plurality of electrodes,
the electrodes comprise a first positive electrode, a second positive electrode, a first negative electrode, and a second negative electrode, the first negative electrode configured to be connected in parallel to the first positive electrode and the second positive electrode through the detection target, the second negative electrode configured to be connected in parallel to the first positive electrode and the second positive electrode through the detection target,
the first positive electrode, the second positive electrode, the first negative electrode, and the second negative electrode are arranged side by side in a direction,
the first positive electrode is closer to an edge of the face than the first negative electrode,
the second positive electrode is farther from the edge of the face than the second negative electrode, and
the second positive electrode and the first negative electrode are arranged between the first positive electrode and the second negative electrode.

12. The electronic device according to claim 1, further comprising:
a determining unit configured to determine, based on an increase in resistance values between the first and second positive electrodes and the first and second negative electrodes, whether or not the electronic device is in a state in which:
any one of the first positive electrode, the second positive electrode, the first negative electrode, and the second negative electrode is separated from the detection target, and the rest of the first positive electrode, the second positive electrode, the first negative electrode, and the second negative electrode are in contact with the detection target, or
one of the first positive electrode and the second positive electrode and one of the first negative electrode and the second negative electrode are separated from the detection target, and the other of the first positive electrode and the second positive electrode and the other of the first negative electrode and the second negative electrode are in contact with the detection target.

13. The electronic device according to claim 1, further comprising:
at least one electric resistor configured to mutually change a resistance value between the first positive electrode and the first negative electrode, a resistance value between the first positive electrode and the second negative electrode, a resistance value between the second positive electrode and the first negative electrode, and a resistance value between the second positive electrode and the second negative electrode.

* * * * *